(12) United States Patent
Smith et al.

(10) Patent No.: US 8,034,558 B2
(45) Date of Patent: Oct. 11, 2011

(54) ACRIDONE DERIVATIVES AS LABELS FOR FLUORESCENCE DETECTION OF TARGET MATERIALS

(75) Inventors: John Anthony Smith, Cardiff (GB); Richard Martin West, Cardiff (GB)

(73) Assignee: GE Healthcare UK Limited, Amersham (GB)

( * ) Notice: Subject to any disclaimer, the term of this patent is extended or adjusted under 35 U.S.C. 154(b) by 787 days.

(21) Appl. No.: 11/943,628

(22) Filed: Nov. 21, 2007

(65) Prior Publication Data

US 2008/0139788 A1    Jun. 12, 2008

Related U.S. Application Data

(63) Continuation of application No. 10/479,578, filed as application No. PCT/GB2002/002509 on May 30, 2002, now abandoned.

(30) Foreign Application Priority Data

Jun. 4, 2001   (GB) .................................. 0113435.2

(51) Int. Cl.
*C12Q 1/68*          (2006.01)
*G01N 33/53*        (2006.01)
*C07H 19/04*       (2006.01)
(52) U.S. Cl. .............. 435/6; 435/7.1; 435/7.2; 536/26.6
(58) Field of Classification Search ................ 435/6, 7.1, 435/7.2; 536/26.6
See application file for complete search history.

(56) References Cited

U.S. PATENT DOCUMENTS 3,021,334 A    2/1962  Smart
(Continued)

FOREIGN PATENT DOCUMENTS

EP            0552108      11/1999
(Continued)

OTHER PUBLICATIONS

Acheson, R M., Constable, E C., Wright, R. G. M. & Taylor, G. N. (1983). "The synthesis of linked acridines as intercalating and antitumour agents". Journal of Chemical Research (S), 2-3.

(Continued)

*Primary Examiner* — Jezia Riley

(57) ABSTRACT

Disclosed are new acridone dye derivatives having characteristic fluorescence lifetimes. Also disclosed are methods for labelling target biological materials employing the acridone dyes and use of the labelled materials in biological assays. The acridone derivatives have the following structure:

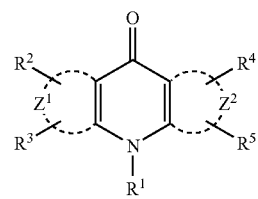

in which $Z^1$ and $Z^2$ represent the atoms necessary to complete one ring, two fused ring, or three fused ring aromatic or heteroaromatic systems, each ring having five or six atoms selected from carbon atoms and optionally no more than two atoms selected from oxygen, nitrogen and sulphur; $R^2$, $R^3$, $R^4$ and $R^5$ are selected from hydrogen, halogen, amide, hydroxyl, cyano, nitro, mono- or di-nitro-substituted benzyl, amino, mono- or di-$C_1$-$C_4$ alkyl-substituted amino, sulphydryl, carbonyl, carboxyl, $C_1$-$C_6$ alkoxy, acrylate, vinyl, styryl, aryl, heteroaryl, $C_1$-$C_{20}$ alkyl, aralkyl, sulphonate, sulphonic acid, quaternary ammonium, the group -E-F and the group —$(CH_2$—$)_n$Y; $R^1$ is selected from hydrogen, mono- or di-nitro-substituted benzyl, $C_1$-$C_{20}$ alkyl, aralkyl, the group -E-F and the group —$(CH_2$—$)_n$Y; where E is a spacer group, F is a target bonding group; Y is selected from sulphonate, sulphate, phosphonate, phosphate, quaternary ammonium and carboxyl; and n is an integer from 1 to 6. The invention also relates to a set of different fluorescent acridone dye derivatives, each dye having a different fluorescence lifetime, the set of dyes being particularly useful for multiparameter analysis.

7 Claims, 6 Drawing Sheets

A = N-(succinyl)-2-amino-10H-acridine-9-one
B = 6-(9-oxo-9H-acridin-10-yl) hexanoic acid
C = 6-(2-bromo-9-oxo-9H-acridin-10-yl) hexanoic acid
D = 6-(9-oxo-9H-acridin-4-carbaxamido) hexanoic acid

U.S. PATENT DOCUMENTS

| | | | |
|---|---|---|---|
| 3,681,360 | A | 8/1972 | Fryer et al. |
| 5,268,486 | A | 12/1993 | Waggoner et al. |
| 5,296,599 | A | 3/1994 | Cohen et al. |
| 5,364,764 | A | 11/1994 | Haugland et al. |
| 5,472,582 | A | 12/1995 | Jackson |
| 5,622,821 | A | 4/1997 | Selvin et al. |
| 5,834,462 | A | 11/1998 | Yoshino et al. |
| 7,105,297 | B2 | 9/2006 | Minshull et al. |

FOREIGN PATENT DOCUMENTS

| | | |
|---|---|---|
| GB | 649147 | 1/1951 |
| GB | 877456 | 9/1961 |
| WO | WO92/11531 | 7/1992 |
| WO | WO97/12872 | 4/1997 |

OTHER PUBLICATIONS

Albert, A. & Ritchie, B. (1942). "9-Aminoacridine". Organic Syntheses, 22, 5-9.

Bahr, N., Tierney, E. & Reymond, J. (Mar. 3, 1997). "Highly photoresistant chemosensors using acridone as fluorescent label". Tetrahedron Letters, 38(9), 1489-1492.

Crisp, G. T. & Gore, J. (Jan. 27, 1997). "Palladium-catalysed attachment of labels with acetylenic linker arms to biological molecules". Tetrahedron, 53(4), 1523-1544.

Crisp, G. T. & Gore, J. (Jan. 27, 1997). "Preparation of biological labels with acetylenic linker arms". Tetrahedron, 53(4), 1505-1522.

Daehne, W. V., Frederiksen, E., Gundersen, E., Lund, F., Moerch, P., Petersen, H. J., Roholt, K., Tybring, L. & Godtfredsen, W. O. (1970). "Acyloxymethyl esters of ampicillin". Journal of Medicinal Chemistry, 13(4), 607-612.

Ebeid, M. Y., El-Moghazy Aly, S. M., Mikhael, A.N. & Eissa, A. A. (1994). "Synthesis and antitumor activity of some acridine—4—yl [n—(p-substituted sulfamoyl)phenyl]carboxamides and their 9—amino derivatives". Journal Bulletin of Faculty of Pharmacy (Cairo University), 32(1), 59-64.

Ege, G., Beisiegel, E. & Arnold, P. (Sep. 1972). "Ringspaltung cyclischer Azoverbindungen, VI. Photolyse von 8-Oxo-8H-chinazolino[3.2-c]1.2.3-benzotriazin Darstellung neuer Diazocine" Chemische Berichte, 105 (9), 2898-2912.

El-Moghazy Aly, S. (1992). "Synthesis and antitumor activity of some 4-(p- substituted phenylaminocarbonylmethyl) acridone carboxylate derivatives". Egyptian Journal of Pharmaceutical Sciences, 33(3-4), 527-538.

Faller, T., Hutton, K., Okafo, G., Gribble, A., Camilleri, P. & Games, D. E. (1997). "A novel acridone derivative for the fluorescence tagging and mass spectrometric sequencing of peptides". Chemical Communications, (16),1529-1530.

Fan, X, You, J., Kang, J., Ou, Q. & Zhu, Q. (Jul. 3, 1998). "New reagents for determination of amino acids by liquid chromatography with pre-column fluorescence derivatization". Analytica Chimica Acta, 367(1-3), 81-91.

He, H. & McGown, L. B. (2000). "DNA sequencing by capillary electrophoresis with four-decay fluorescence detection". Analytical Chemistry, 72(24), 5865-5873.

Jansen, A. B. A. & Russell, T. J. (1965). "379. Some novel penicillin derivatives". Journal of the Chemical Society, 2127-2132.

Lakowicz, J. R. (1999). "Principles of Fluorescence Spectroscopy". 2nd ed. New York: Springer/Kluwer Academic/Plenum Publishers.

Madhu, C., Rix, P., Nguyen, T., Chien, D., Woodward, D. & Tang-Liu, D. D.-S. (1998). "Penetration of Natural Prostaglandins and Their Ester Prodrugs and Analogs Across Human Ocular Tissues In Vitro". Journal of Ocular Pharmacology and Therapeutics, 14(5), 389-399.

Miosga, N., Romer, W. & Letsch, G. (1985). "Fluorimetric Characterization and TLC of Some Acridanone Derivatives". Pharmazie, 40(11), 800-801.

Naylor, L. H. (Sep. 1, 1999). "Reporter gene technology: the future looks bright". Biochemical Pharmacology, 58(5), 749-757.

Reymond, J.-L., Koch, T., Schröer, J. & Tierney, E. (Apr. 30, 1996). "A general assay for antibody catalysis using acridone as a fluorescent tag". Proceedings of the National Academy of Sciences, 93(9), 4251-4256.

Sauer, M., Han, K.-T., Müller, R., Schulz, A., Tadday, R., Seeger, S., Wolfrum, J., Arden-Jacob, J., Deltau, G., Marx, N. J. & Drexhage, K. H. (Sep. 1993). "New fluorescent labels for time-resolved detection of biomolecules". Journal of Fluorescence, 3(3), 131-139.

Schofield, P. C., Robertson, I. G. C., Paxton, J. W., McCrystal, M. R., Evans, B. D., Kestell, P. & Baguley, B. C. (May 1999). "Metabolism of N-[2-(dimethylamino)ethyl]acridine-4-carboxamide in cancer patients undergoing a phase I clinical trial". Journal Cancer Chemotherapy and Pharmacology, 44(1) 51-58.

Suzuki, N., Itagaki, T., Goto, A., Yoda, B., Nomoto, T., Mizumoto, I., Inaba, H. & Goto, T. (1991). "Studies on the chemiluminescent detection of active oxygen species: 9-acridone-2-sulfonic acid, a specific probe for supexaxide". Agricultural and Biological Chemistry, 55(6), 1561-1564.

Szulc, Z. (1987). "Synthesis of halogen derivatives of 9-oxo-10-acridineacetic acid as potential interferon inducers". Journal für Praktische Chemie, 329(4), 741-744.

Szymanska, A., Wiczk, W. & Lankiewicz, L. (Jul. 2000). "Synthesis and photophysics of acridine derivatives". Journal Chemistry of Heterocyclic Compounds, 36(7), 801-808.

Ullmann, F. (1903). Chemische Berichte, 36, 2382.

Val'Kova, G. A., Shcherbo, S. N. & Shigorin, D. N. (1978). "On the classification of molecules in terms if their luminescence spectra II". New York, NY: Plenum Publishing Corp, pp. 491-493.

You, J., Lao, W., You, J. & Wang, G. (1999). "Characterization and application of acridine-9-N-acetyl-N-hydroxysuccinimide as a pre-column derivatization agent for fluorimetric detection of amino acids in liquid chromatography". The Analyst, 124(12), 1755-1760.

You, J., Sun, X., Lao, W., Ou, Q. & Jiang, D. (May 26, 1999). "Derivatization of alcohols using acridone-9-N-acetyl-benzenedisulfonate as a condensation agent and its application for the determination of volatile alcohols in human plasma by liquid chromatography with fluorescence detection". Analytica Chimica Acta, 391(1), 43-55.

Geymayer, et al., Chem. Eur. J., 5(3):1006-1012 (1999).

——— N-(succinyl)-2-amino-10H-acridine-9-one
·········· 6-(9-oxo-9H-acridin-10-yl)hexanoic acid
— — — 6-(2-bromo-9-oxo-9H-acridin-10-yl)hexanoic acid
— ·· — · 6-(9-oxo-9H-acridin-4-carbaxamido)hexanoic acid A = N-(succinyl)-2-amino-10H-acridine-9-one
B = 6-(9-oxo-9H-acridin-10-yl) hexanoic acid
C = 6-(2-bromo-9-oxo-9H-acridin-10-yl) hexanoic acid
D = 6-(9-oxo-9H-acridin-4-carbaxamido) hexanoic acid A = 6-(9-oxo-9H-acridin-10-yl)hexanoic acid - bovine serum albumin (BSA) conjugate (conjugate 1)

B = 6-(9-oxo-9H-acridin-4-carbaxamido)hexanoic acid - rabbit serum albumin conjugate (conjugate 2)

Immunoprecipitation using anti-BSA antibody

A = Initial Mixture
B = Immunoprecipitated pellet (re-suspended in 0.1M NaOH for lifetime determination)
C = Supernatant

ACRIDONE DERIVATIVES AS LABELS FOR FLUORESCENCE DETECTION OF TARGET MATERIALS

CROSS-REFERENCE TO RELATED APPLICATIONS

This application is a continuation of U.S. patent application Ser. No. 10/479,578 filed Dec. 1, 2003, abandoned, which is a filing under 35 U.S.C. §371 and claims priority to international patent application number PCT/GB2002/002509 filed May 30, 2002, published on Dec. 12, 2002, as WO 2002/099424, which claims priority to patent application number GB 0113435.2 filed Jun. 4, 2001.

BACKGROUND OF THE INVENTION

1. Field of the Invention

The present invention relates to new acridone derivatives having characteristic fluorescence lifetimes that can be used as labels for attachment to and labelling of target materials. The acridone derivatives of the invention may be easily distinguished, one from the other, by virtue of their fluorescence lifetimes and they may be used in multiparameter applications. The invention also relates to assay methods utilising acridone derivatives and to a set of different fluorescent acridone lifetime dyes.

2. Description of the Prior Art

There is an increasing interest in, and demand for, fluorescent labels for use in the labelling and detection of biological materials. Fluorescent labels are generally stable, sensitive and a wide range of methods are now available for the labelling of biomolecules. Typically, the emission spectrum of a fluorescent dye is a characteristic property of the dye, the intensity of such emission being used in the detection of materials labelled with that dye. One problem with measurements of fluorescence intensity as a means of detecting and/or measuring the concentration of a fluorescent labelled biomolecule is that background fluorescence may interfere with the measurement. Thus, in order to obtain improvements in the sensitivity of fluorescence detection, it is highly desirable to improve the signal-to-noise ratio.

One means of overcoming the problem of background noise has been through the use of long wavelength dyes, for example, the cyanine dyes Cy™5 and Cy7, as disclosed in U.S. Pat. No. 5,268,486 (Waggoner et al). These dyes emit in the 600-800 nm region of the spectrum, where background fluorescence is much less of a problem. Another means of improving the signal-to-noise ratio in fluorescence measurements is in the use of time-resolved fluorescence, for example by using fluorescent labels based on lanthanide chelates, eg. $Eu^{3+}$ and $Tb^{3+}$ (Selvin et al, U.S. Pat. No. 5,622,821). In time-resolved fluorescent labels, the lifetime of the fluorescence emission is typically longer than that of the background fluorescence, which may therefore be gated out using appropriate instrumentation.

McGown, L. B. et al (Anal. Chem., (2000), 72, 5865-73) describe the use of a range of different dyes for multiparameter analysis in which fluorescence lifetime, rather than fluorescence wavelength, is the discriminating characteristic. Dyes from different dye classes were used to obtain lifetime resolution; however compensation was required for either mobility differences or different fluorescence signal intensities. The method has been refined by Sauer, M. et al (J. Fluorescence, (1993), 3(3), 131-139) who employed a series of rhodamine-based fluors having a range of fluorescent lifetimes but which all absorb and emit at similar wavelengths, thus avoiding having to change the excitation source and emission filters.

The acridone chromophore is highly fluorescent and has been used for labelling biological molecules and subsequent detection by conventional fluorescence emission spectroscopy. For example, Faller, T. et al (J. Chem. Soc. Chem. Comm., (1997), 1529-30) describe the preparation of a succinimidyl ester derivative of acridone and its use in labelling peptides for subsequent analysis by mass-spectroscopy. U.S. Pat. No. 5,472,582 (Jackson) describes the use of the fluorescent label, 2-aminoacridone, for labelling and detecting carbohydrates in a mixture, following electrophoretic separation.

Val'kova, G. et al (Dokl. Akad. Nauk. SSR, (1978), 240(4), 884-7) have measured the fluorescence lifetimes of several acridone derivatives, however, to date, there appear to be no reports relating to the use of acridones as lifetime dyes suitable for labelling and the detection of biological materials.

SUMMARY OF THE INVENTION

The present invention therefore describes modifications of the acridone chromophore, to produce a range of acridone derivatives having characteristic fluorescence lifetimes and which are useful for labelling biological materials.

The acridone derivatives of the present invention moreover provide a valuable set of fluorescent labels having a common core structure and which are particularly useful for multiparameter analysis. In each dye of a set of dyes, the absorption and emission spectra remain essentially the same, whilst the fluorescence lifetimes vary. Thus, it is possible to use a common excitation source and determine the lifetimes at the same emission wavelength, thereby simplifying requirements for detection instrumentation used in multiparameter experiments. Another advantage of the present invention is that the fluorescence lifetimes of the acridone dye derivatives are generally longer than the lifetimes of other fluorescent labels, as well as naturally occurring fluorescent materials, such as proteins and polynucleotides, thereby allowing easy discrimination from background fluorescence in biological assays utilising such dyes.

Accordingly, in a first aspect of the present invention there is provided use of a reagent for labelling and lifetime detection of a target material, wherein said reagent is a dye of the formula (I):

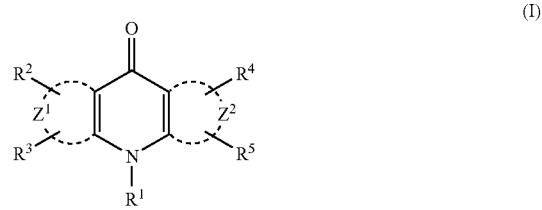

wherein:
groups $R^2$ and $R^3$ are attached to the $Z^1$ ring structure and groups $R^4$ and $R^5$ are attached to the $Z^2$ ring structure;
$Z^1$ and $Z^2$ independently represent the atoms necessary to complete one ring, two fused ring, or three fused ring aromatic or heteroaromatic systems, each ring having five or six atoms selected from carbon atoms and optionally no more than two atoms selected from oxygen, nitrogen and sulphur;

$R^2$, $R^3$, $R^4$ and $R^5$ are independently selected from hydrogen, halogen, amide, hydroxyl, cyano, nitro, mono- or di-nitro-substituted benzyl, amino, mono- or di-$C_1$-$C_4$ alkyl-substituted amino, sulphydryl, carbonyl, carboxyl, $C_1$-$C_6$ alkoxy, acrylate, vinyl, styryl, aryl, heteroaryl, $C_1$-$C_{20}$ alkyl, aralkyl, sulphonate, sulphonic acid, quaternary ammonium, the group -E-F and the group —$(CH_2$—$)_n Y$;

$R^1$ is selected from hydrogen, mono- or di-nitro-substituted benzyl, $C_1$-$C_{20}$ alkyl, aralkyl, the group -E-F and the group —$(CH_2$—$)_n Y$;

E is a spacer group having a chain from 1-60 atoms selected from the group consisting of carbon, nitrogen, oxygen, sulphur and phosphorus atoms and F is a target bonding group;

Y is selected from sulphonate, sulphate, phosphonate, phosphate, quaternary ammonium and carboxyl; and n is an integer from 1 to 6.

In a first embodiment of the first aspect, the dye of formula (I) is a fluorescent dye wherein:

groups $R^2$ and $R^3$ are attached to the $Z^1$ ring structure and groups $R^4$ and $R^5$ are attached to the $Z^2$ ring structure, where $Z^1$ and $Z^2$ are hereinbefore defined;

$R^2$, $R^3$, $R^4$ and $R^5$ are independently selected from hydrogen, halogen, amide, hydroxyl, cyano, amino, mono- or di-$C_1$-$C_4$ alkyl-substituted amino, sulphydryl, carbonyl, carboxyl, $C_1$-$C_6$ alkoxy, acrylate, vinyl, styryl, aryl, heteroaryl, $C_1$-$C_{20}$ alkyl, aralkyl, sulphonate, sulphonic acid, quaternary ammonium, the group -E-F and the group —$(CH_2$—$)_n Y$; and $R^1$ is selected from hydrogen, $C_1$-$C_{20}$ alkyl, aralkyl, the group -E-F and the group —$(CH_2$—$)_n Y$;

wherein E, F, Y and n are hereinbefore defined.

The acridone dyes according to the first embodiment of the first aspect are particularly suitable for use as fluorescence lifetime dyes. In the context of the present invention, the term lifetime dye is intended to mean a dye having a measurable fluorescence lifetime, defined as the average amount of time that the dye remains in its excited state following excitation (Lackowicz, J. R., Principles of Fluorescence Spectroscopy, Kluwer Academic/Plenum Publishers, New York, (1999)).

Preferably, the fluorescent dye has a fluorescence lifetime in the range from 2 to 30 nanoseconds, more preferably from 2 to 20 nanoseconds.

In a second embodiment of the first aspect, the dye of formula (I) is a non-fluorescent or substantially non-fluorescent dye wherein:

groups $R^1$, $R^2$, $R^3$, $R^4$, $R^5$, $Z^1$ and $Z^2$ are hereinbefore defined; and wherein at least one of groups $R^1$, $R^2$, $R^3$, $R^4$ and $R^5$ comprises at least one nitro group.

In this embodiment, suitably, the at least one nitro group may be attached directly to the $Z^1$ and/or $Z^2$ ring structures. In the alternative, a mono- or di-nitro-substituted benzyl group may be attached to the $R^1$, $R^2$, $R^3$, $R^4$ or $R^5$ positions, which optionally may be further substituted with one or more nitro groups attached directly to the $Z^1$ and/or $Z^2$ ring structures.

Preferably, in the first and second embodiments, at least one of groups $R^1$, $R^2$, $R^3$, $R^4$ and $R^5$ in the dye of formula (I) is the group -E-F where E and F are hereinbefore defined.

Suitably, the target bonding group F is a reactive or functional group. A reactive group of a compound according to formula (I) can react under suitable conditions with a functional group of a target material; a functional group of a compound according to formula (I) can react under suitable conditions with a reactive group of the target material such that the target material becomes labelled with the compound.

Preferably, when F is a reactive group, it is selected from succinimidyl ester, sulpho-succinimidyl ester, isothiocyanate, maleimide, haloacetamide, acid halide, vinylsulphone, dichlorotriazine, carbodiimide, hydrazide and phosphoramidite. Preferably, when F is a functional group, it is selected from hydroxy, amino, sulphydryl, imidazole, carbonyl including aldehyde and ketone, phosphate and thiophosphate. By virtue of these reactive and functional groups the compounds of formula (I) may be reacted with and covalently bond to target materials.

Suitably, $Z^1$ and $Z^2$ may be selected independently from the group consisting of phenyl, pyridinyl, naphthyl, anthranyl, indenyl, fluorenyl, quinolinyl, indolyl, benzothiophenyl, benzofuranyl and benzimidazolyl moieties. Additional one, two fused, or three fused ring systems will be readily apparent to the skilled person. Preferably, $Z^1$ and $Z^2$ are selected from the group consisting of phenyl, pyridinyl, naphthyl, quinolinyl and indolyl moieties. Particularly preferred $Z^1$ and $Z^2$ are phenyl and naphthyl moieties.

Preferably, at least one of the groups $R^1$, $R^2$, $R^3$, $R^4$ and $R^5$ of the dyes of formula (I) is a water solubilising group for conferring a hydrophilic characteristic to the compound. Solubilising groups, for example, sulphonate, sulphonic acid and quaternary ammonium, may be attached directly to the aromatic ring structures $Z^1$ and/or $Z^2$ of the compound of formula (I). Alternatively, solubilising groups may be attached by means of a $C_1$ to $C_6$ alkyl linker chain to said aromatic ring structures and may be selected from the group —$(CH_2$—$)_n Y$ where Y is selected from sulphonate, sulphate, phosphonate, phosphate, quaternary ammonium and carboxyl; and n is an integer from 1 to 6. Alternative solubilising groups may be carbohydrate residues, for example, monosaccharides. Examples of water solubilising constituents include $C_1$-$C_6$ alkyl sulphonates, such as —$(CH_2)_3$—$SO_3^-$ and —$(CH_2)_4$—$SO_3^-$. However, one or more sulphonate or sulphonic acid groups attached directly to the aromatic ring structures of a dye of formula (I) are particularly preferred. Water solubility may be advantageous when labelling proteins.

Suitable spacer groups E may contain 1-60 chain atoms selected from the group consisting of carbon, nitrogen, oxygen, sulphur and phosphorus. For example the spacer group may be:

—$(CHR')_p$—

—$\{(CHR')_q$—O—$(CHR')_r\}_s$—

—$\{(CHR')_q$—S—$(CHR')_r\}_s$—

—$\{(CHR')_q$—NR'—$(CHR')_r\}_s$—

—$\{(CHR')_q$—(CH=CH)—$(CHR')_r\}_s$—

—$\{(CHR')_q$—Ar—$(CHR')_r\}_s$—

—$\{(CHR')_q$—CO—NR'—$(CHR')_r\}_s$—

—$\{(CHR')_q$—CO—Ar—NR'—$(CHR')_r\}_s$— where R' is hydrogen, $C_1$-$C_4$ alkyl or aryl, which may be optionally substituted with sulphonate, Ar is phenylene, optionally substituted with sulphonate, p is 1-20, preferably 1-10, q is 0-10, r is 1-10 and s is 1-5.

Specific examples of reactive groups $R^1$, $R^2$, $R^3$, $R^4$ and $R^5$ and the groups with which $R^1$, $R^2$, $R^3$, $R^4$ and $R^5$ can react are provided in Table 1. In the alternative, groups $R^1$, $R^2$, $R^3$, $R^4$ and $R^5$ may be the functional groups of Table 1 that would react with the reactive groups of a target material.

TABLE 1

Possible Reactive Substituents and Sites Reactive Therewith

| Reactive Groups | Functional Groups |
| --- | --- |
| succinimidyl esters | primary amino, secondary amino |
| isothiocyanates | amino groups |
| haloacetamides, maleimides | sulphydryl, imidazole, hydroxyl, amine |
| acid halides | amino groups |
| anhydrides | primary amino, secondary amino, hydroxyl |
| hydrazides, | aldehydes, ketones |
| vinylsulphones | amino groups |
| dichlorotriazines | amino groups |
| carbodiimides | carboxyl groups |
| phosphoramidites | hydroxyl groups |

Preferred reactive groups which are especially useful for labelling target materials with available amino and hydroxyl functional groups include:

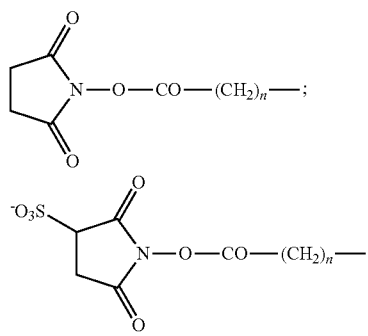

where n is 0 or an integer from 1-10.

Aryl is an aromatic substituent containing one or two fused aromatic rings containing 6 to 10 carbon atoms, for example phenyl or naphthyl, the aryl being optionally and independently substituted by one or more substituents, for example halogen, hydroxyl, straight or branched chain alkyl groups containing 1 to 10 carbon atoms, aralkyl and $C_1$-$C_6$ alkoxy, for example methoxy, ethoxy, propoxy and n-butoxy.

Heteroaryl is a mono- or bicyclic 5 to 10 membered aromatic ring system containing at least one and no more than 3 heteroatoms which may be selected from N, O, and S and is optionally and independently substituted by one or more substituents, for example halogen, hydroxyl, straight or branched chain alkyl groups containing 1 to 10 carbon atoms, aralkyl and $C_1$-$C_6$ alkoxy, for example methoxy, ethoxy, propoxy and n-butoxy.

Aralkyl is a $C_1$ to $C_6$ alkyl group substituted by an aryl or heteroaryl group.

Halogen and halo groups are selected from fluorine, chlorine, bromine and iodine.

Exemplary dyes according to the first embodiment of the first aspect are as follows:
i) O—(N-succinimidyl)-6-(9-oxo-9H-acridin-10-yl)hexanoate
ii) O—(N-succinimidyl)-6-(2-bromo-9-oxo-9H-acridin-10-yl)hexanoate
iii) O—(N-succinimidyl)-6-(9-oxo-9H-acridin-4-carboxamido)hexanoate
iv) O—(N-succinimidyl)-6-(2-acetamido-9-oxo-9H-acridin-10-yl)hexanoate.

The dyes of the present invention may be used to label and thereby impart fluorescent properties to a variety of target biological materials. Thus, in a second aspect, there is provided a method for labelling a target biological material, the method comprising:

i) adding to a liquid containing said target biological material a dye of formula (I):

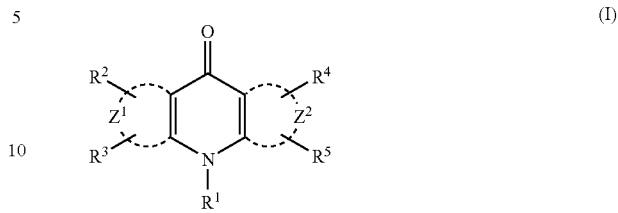

wherein:
groups $R^2$ and $R^3$ are attached to the $Z^1$ ring structure and groups $R^4$ and $R^5$ are attached to the $Z^2$ ring structure, where $Z^1$ and $Z^2$ are hereinbefore defined;
$R^2$, $R^3$, $R^4$ and $R^5$ are independently selected from hydrogen, halogen, amide, hydroxyl, cyano, amino, mono- or di-$C_1$-$C_4$ alkyl-substituted amino, sulphydryl, carbonyl, carboxyl, $C_1$-$C_6$ alkoxy, acrylate, vinyl, styryl, aryl, heteroaryl, $C_1$-$C_{20}$ alkyl, aralkyl, sulphonate, sulphonic acid, quaternary ammonium, the group -E-F and the group —$(CH_2—)_n Y$;
$R^1$ is selected from hydrogen, $C_1$-$C_{20}$ alkyl, aralkyl, the group -E-F and the group —$(CH_2—)_n Y$;
where E, F, Y and n are hereinbefore defined; and
ii) incubating said dye with said target biological material under conditions suitable for labelling said target.

Suitably, the fluorescent dyes of the present invention wherein at least one of the groups $R^1$ to $R^5$ contains a charge, for example, quaternary amino, may be used to bind non-covalently to charged biological molecules such as, for example, DNA and RNA. Alternatively, fluorescent dyes of the present invention wherein at least one of the groups $R^1$ to $R^5$ is an uncharged group, for example, a long chain alkyl or an aryl group, may be used to bind to uncharged biological molecules such as, for example, biological lipids, as well as to intact cell membranes, membrane fragments and cells.

In a preferred embodiment, at least one of the groups $R^1$, $R^2$, $R^3$, $R^4$ and $R^5$ in the dye of formula (I) is the group -E-F where E and F are hereinbefore defined. In this embodiment, the fluorescent dyes may be used to covalently label a target biological material. The target bonding group may be a reactive group for reacting with a functional group of the target material. Alternatively, the target bonding group may be a functional group for reacting with a reactive group on the target biological material. The method comprises incubating the target material with an amount of the dye according to the invention under conditions to form a covalent linkage between the target and the dye. The target may be incubated with an amount of a compound according to the present invention having at least one of groups $R^1$, $R^2$, $R^3$, $R^4$ and $R^5$ that includes a reactive or functional group as hereinbefore defined that can covalently bind with the functional or reactive group of the target biological material.

Suitable biological materials include, but are not limited to the group consisting of antibody, lipid, protein, peptide, carbohydrate, nucleotides which contain or are derivatized to contain one or more of an amino, sulphydryl, carbonyl, hydroxyl and carboxyl, phosphate and thiophosphate groups, and oxy or deoxy polynucleic acids which contain or are derivatized to contain one or more of an amino, sulphydryl, carbonyl, hydroxyl and carboxyl, phosphate and thiophosphate groups, microbial materials, drugs, hormones, cells, cell membranes and toxins.

The fluorescent dyes according to the invention having a target bonding group in at least one of groups $R^1$, $R^2$, $R^3$, $R^4$ and $R^5$ may be used in an assay method for determining the presence or the amount of an analyte in a sample. Thus, in a third aspect of the present invention, there is provided a method for the assay of an analyte in a sample which method comprises:

i) contacting the analyte with a specific binding partner for said analyte under conditions suitable to cause the binding of at least a portion of said analyte to said specific binding partner to form a complex and wherein one of said analyte and said specific binding partner is labelled with a fluorescent dye of formula (I):

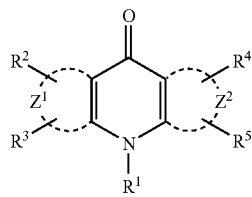

(I)

wherein:
groups $R^2$ and $R^3$ are attached to the $Z^1$ ring structure and groups $R^4$ and $R^5$ are attached to the $Z^2$ ring structure, where $Z^1$ and $Z^2$ are hereinbefore defined;
at least one of groups $R^1$, $R^2$, $R^3$, $R^4$ and $R^5$ is the group -E-F where E is a spacer group having a chain from 1-60 atoms selected from the group consisting of carbon, nitrogen, oxygen, sulphur and phosphorus atoms and F is a target bonding group;
when any of said groups $R^2$, $R^3$, $R^4$ and $R^5$ is not said group -E-F, said remaining groups $R^2$, $R^3$, $R^4$ and $R^5$ are independently selected from hydrogen, halogen, amide, hydroxyl, cyano, amino, mono- or di-$C_1$-$C_4$ alkyl-substituted amino, sulphydryl, carbonyl, carboxyl, $C_1$-$C_6$ alkoxy, acrylate, vinyl, styryl, aryl, heteroaryl, $C_1$-$C_{20}$ alkyl, aralkyl, sulphonate, sulphonic acid, quaternary ammonium and the group —$(CH_2$—$)_n Y$; and,
when group $R^1$ is not said group -E-F, it is selected from hydrogen, $C_1$-$C_{20}$ alkyl, aralkyl and the group —$(CH_2$—$)_n Y$;
wherein Y and n are hereinbefore defined;
ii) measuring the emitted fluorescence of the labelled complex; and
iii) correlating the emitted fluorescence with the presence or the amount of said analyte in said sample.

Suitably, step ii) may be performed by measurement of the fluorescence intensity or fluorescence lifetime of the sample, preferably the fluorescence lifetime.

In one embodiment, the assay method is a direct assay for the measurement of an analyte in a sample. Optionally, a known or putative inhibitor compound may be included in the assay mix.

In a second, or alternative embodiment, the assay may be a competitive assay wherein a sample containing an analyte competes with a fluorescent tracer for a limited number of binding sites on a binding partner that is capable of specifically binding the analyte and the tracer. Suitably, the tracer is a labelled analyte or a labelled analyte analogue, in which the label is a fluorescent dye of formula (I). Increasing amounts (or concentrations) of the analyte in the sample will reduce the amount of the fluorescent labelled analyte or fluorescent labelled analyte analogue that is bound to the specific binding partner. The fluorescence signal is measured and the concentration of analyte may be obtained by interpolation from a standard curve.

In a further embodiment, the binding assay may employ a two-step format, wherein a first component (which may be optionally coupled to an insoluble support) is bound to a second component to form a specific binding complex, which is bound in turn to a third component. In this format, the third component is capable of specifically binding to either the second component, or to the specific binding complex. Either of the second or the third component may be labelled with a fluorescent dye according to the present invention. Examples include "sandwich" assays, in which one component of a specific binding pair, such as a first antibody, is coated onto a surface, such as the wells of a multiwell plate. Following the binding of an antigen to the first antibody, a fluorescent labelled second antibody is added to the assay mix, so as to bind with the antigen-first antibody complex. The fluorescence signal is measured and the concentration of antigen may be obtained by interpolation from a standard curve.

Examples of analyte-specific binding partner pairs include, but are not restricted to, antibodies/antigens, lectins/glycoproteins, biotin/streptavidin, hormone/receptor, enzyme/substrate or co-factor, DNA/DNA, DNA/RNA and DNA/binding protein. It is to be understood that any molecules which possess a specific binding affinity for each other may be employed, so that the fluorescent dyes of the present invention may be used for labelling one component of a specific binding pair, which in turn may be used in the detection of binding to the other component.

The fluorescent dyes according to first embodiment of the first aspect may be used in applications that include detecting and distinguishing between various components in a mixture. Thus, in a fourth aspect, the present invention provides a set of two or more different fluorescent dyes according to the invention, each dye of said set of dyes having the formula (I):

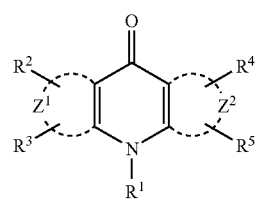

(I)

wherein:
groups $R^2$ and $R^3$ are attached to the $Z^1$ ring structure and groups $R^4$ and $R^5$ are attached to the $Z^2$ ring structure, where $Z^1$ and $Z^2$ are hereinbefore defined;
$R^2$, $R^3$, $R^4$ and $R^5$ are independently selected from hydrogen, halogen, amide, hydroxyl, cyano, amino, mono- or di-$C_1$-$C_4$ alkyl-substituted amino, sulphydryl, carbonyl, carboxyl, $C_1$-$C_6$ alkoxy, acrylate, vinyl, styryl, aryl, heteroaryl, $C_1$-$C_{20}$ alkyl, aralkyl, sulphonate, sulphonic acid, quaternary ammonium, the group -E-F and the group —$(CH_2$—$)_n Y$;
$R^1$ is selected from hydrogen, $C_1$-$C_{20}$ alkyl, aralkyl, the group -E-F and the group —$(CH_2$—$)_n Y$;
E is a spacer group having a chain from 1-60 atoms selected from the group consisting of carbon, nitrogen, oxygen, sulphur and phosphorus atoms and F is a target bonding group;
Y is selected from sulphonate, sulphate, phosphonate, phosphate, quaternary ammonium and carboxyl; and n is an integer from 1 to 6;

wherein each dye of said set has a distinguishably different fluorescence lifetime compared with the lifetimes of the remaining dyes of the set.

Preferably, in each dye of the set of dyes at least one of groups $R^1$, $R^2$, $R^3$, $R^4$ and $R^5$ is the group -E-F where E and F are hereinbefore defined.

Preferably, the set of fluorescent dyes according to the invention will comprise four different dyes, each dye of the set having a different fluorescence lifetime.

Preferably, each of the fluorescent dyes in the set has a fluorescence lifetime in the range from 2 to 30 nanoseconds. More preferably the fluorescent dyes in the set will have fluorescence lifetimes in the range from 2 to 20 nanoseconds.

To distinguish between different dyes in the set of dyes, the difference in the lifetimes of the fluorescent emission of two such dyes is preferably at least 15% of the value of the shorter lifetime dye.

The set of dyes may be used in a detection method wherein different fluorescent dyes of the set of dyes are covalently bonded to a plurality of different primary components, each primary component being specific for a different secondary component, in order to identify each of a plurality of secondary components in a mixture of secondary components. The method comprises covalently binding different dyes of a set of fluorescent dyes according to the fourth aspect of the invention to different primary components in a multicomponent mixture wherein each dye of the set has a different fluorescence lifetime, compared with the fluorescence lifetimes of the remaining dyes of the set; adding the dye-labelled primary components to a preparation containing secondary components under conditions to enable binding of at least a portion of each of said dye-labelled primary components to its respective secondary component; and determining the presence or the amount of the bound secondary component by measuring the fluorescence lifetime of each of the labelled primary component-secondary component complexes.

If required, any unreacted primary components may be removed or separated from the preparation by, for example washing, to prevent interference with the analysis.

Preferably, a single wavelength of excitation can be used to excite fluorescence from two or more materials in a mixture, where each fluoresces having a different characteristic fluorescent lifetime.

The set of fluorescent dyes according to the present invention may be used in any system in which the creation of a fluorescent primary component is possible. For example, an appropriately reactive fluorescent dye according to the invention can be conjugated to a DNA or RNA fragment and the resultant conjugate then caused to bind to a complementary target strand of DNA or RNA. Other examples of primary component-secondary component complexes which may be detected include antibodies/antigens and biotin/streptavidin.

The set of dyes according to the present invention may also be advantageously used in fluorescent DNA sequencing based upon fluorescence lifetime discrimination of the DNA fragments. Briefly, each one of a set of dyes, may be coupled to a primer. Various primers are available, such as primers from pUC/M13, λgt10, λgt11 and the like (see Sambrook et al, Molecular Cloning, A Laboratory Manual 2$^{nd}$ Edition, Cold Spring Harbour Laboratory Press 1989). DNA sequences are cloned into an appropriate vector having a primer sequence joined to the DNA fragment to be sequenced. After hybridisation to the DNA template, polymerase enzyme-directed synthesis of a complementary strand occurs. Different 2',3'-dideoxynucleotide terminators are employed in each different sequencing reaction so as to obtain base-specific termination of the chain extension reaction. The resulting set of DNA fragments are separated by electrophoresis and the terminating nucleotide (and thus the DNA sequence) is determined by detecting the fluorescence lifetime of the labelled fragments. DNA sequencing may also be performed using dideoxynucleotide terminators covalently labelled with the fluorescent dyes according to the present invention.

The non-fluorescent or substantially non-fluorescent dyes according to the second embodiment of the first aspect may be used as the substrate for an enzyme and which upon reaction with the enzyme, yields a fluorescent product.

Bacterial nitroreductases have been shown to catalyse the general reaction set out below in Reaction Scheme 1.

Reaction Scheme 1

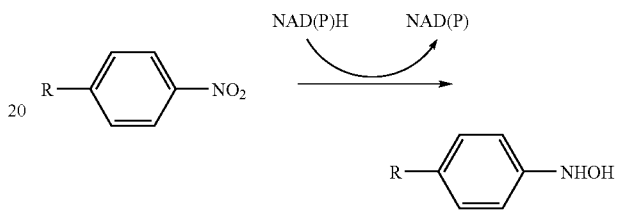

where, in the presence of NADH or NADPH, one or more nitro groups on an organic molecule may be reduced to a hydroxylamine (—NHOH) group which may subsequently be converted to an amine (—NH$_2$) group.

Thus, in a fifth aspect of the invention, there is provided a method of increasing the fluorescence of a dye of formula (I):

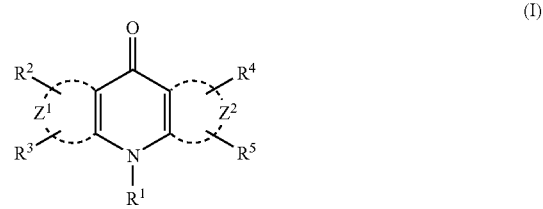

(I)

wherein:
groups $R^1$, $R^2$, $R^3$, $R^4$, $R^5$, $Z^1$ and $Z^2$ are hereinbefore defined and wherein at least one of groups $R^1$, $R^2$, $R^3$, $R^4$ and $R^5$ comprises at least one nitro group;
characterised by the reduction of said at least one nitro group to —NHOH or —NH$_2$ Preferably, the fluorescence lifetime of the fluorescent product of the reduction is in the range from 2 to 30 nanoseconds.

Suitably, reduction is by means of nitroreductase. This can be achieved by enzymatic conversion of a nitro group in a compound of formula (I) to a —NHOH or —NH$_2$ group by the action of the nitroreductase. Depending on the structure of the dye, the fluorescence emission from the product of the nitroreductase reaction may typically have a lifetime in the range 2 to 30 nanoseconds. Moreover, the fluorescence lifetime characteristics of the reaction product can be altered to suit the application by means of additional substitutents, whilst retaining the nitro group(s) that are involved in the reaction with nitroreductase. Thus, fluorescent reporters compatible for use with other fluors in multiplex systems can be provided.

In a sixth aspect of the invention there is provided a method for detecting nitroreductase enzyme activity in a composition comprising:

i) mixing under conditions to promote nitroreductase activity said composition with a dye of formula (I):

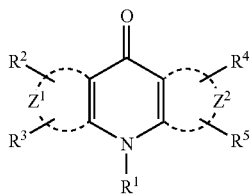

wherein:
groups $R^1$, $R^2$, $R^3$, $R^4$, $R^5$, $Z^1$ and $Z^2$ are hereinbefore defined and wherein at least one of groups $R^1$, $R^2$, $R^3$, $R^4$ and $R^5$ comprises at least one nitro group; and
ii) measuring an increase in fluorescence wherein said increase is a measure of the amount of nitroreductase activity.

Suitably, the measurement of step ii) may be of the fluorescence intensity and/or fluorescence lifetime of the dye.

In one embodiment of the sixth aspect, the composition comprises a cell or cell extract. In principle, any type of cell can be used, i.e. prokaryotic or eukaryotic (including bacterial, mammalian and plant cells). Where appropriate, a cell extract can be prepared from a cell, using standard methods known to those skilled in the art (Molecular Cloning, A Laboratory Manual $2^{nd}$ Edition, Cold Spring Harbour Laboratory Press 1989), prior to measuring fluorescence.

Typical conditions for nitroreductase activity comprise incubation of the composition in a suitable medium and the dye at approximately 37° C. in the presence of NADH and FMN.

In a seventh aspect of the invention there is provided an assay method comprising:
i) binding one component of a specific binding pair to a surface;
ii) adding a second component of the specific binding pair under conditions to promote binding between the components, said second component being labelled with a nitroreductase enzyme;
iii) adding a dye of formula (I):

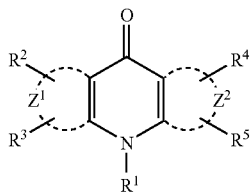

wherein:
groups $R^1$, $R^2$, $R^3$, $R^4$, $R^5$, $Z^1$ and $Z^2$ are hereinbefore defined and wherein at least one of groups $R^1$, $R^2$, $R^3$, $R^4$ and $R^5$ comprises at least one nitro group; and
iv) detecting binding of the second component to the first component by measuring an increase in fluorescence as a measure of bound nitroreductase activity.

In a preferred embodiment of the seventh aspect, said specific binding pair is selected from the group consisting of antibodies/antigens, lectins/glycoproteins, biotin/streptavidin, hormone/receptor, enzyme/substrate, DNA/DNA, DNA/RNA and DNA/binding protein.

Briefly, an in vitro assay method for the detection of antibody binding may be configured as follows. An antibody specific for an antigen of interest may be labelled by covalently linking it to an enzymatically active nitroreductase. The labelled antibody can then be introduced into the test sample containing the antigen under conditions suitable for binding. After washing to remove any unbound antibody, the amount of bound antibody is detected by incubating the sample with a substrate comprising a compound of formula (I) having at least one nitro group under conditions for nitroreductase activity and measuring an increase in fluorescence. The amount of fluorescence detected will be proportional to the amount of nitroreductase-labelled antibody that has bound to the antigen.

In an in vitro assay for detecting the binding of nucleic acids by hybridisation, either of the pair of target and probe nucleic acid is immobilised by attachment to a membrane or surface. The second member of the pair is labelled with nitroreductase and incubated under hybridising conditions with the immobilised nucleic acid. Unbound, labelled nucleic acid is washed off and the amount of bound, labelled nucleic acid is measured by incubating the membrane or surface with a compound of formula (I) having at least one nitro group under conditions suitable for nitroreductase activity. The amount of increase in fluorescence gives a measure of the amount of bound labelled DNA.

Methods for coupling enzymes, such as nitroreductase, to other biomolecules, e.g. proteins and nucleic acids, are well known (Bioconjugate Techniques, Academic Press 1996). Coupling may be achieved by direct means, for example by use of a suitable bifunctional crosslinking agent (e.g. N-[γ-maleimidopropionic acid]hydrazine, Pierce) to covalently link the enzyme and binding partner. Alternatively, coupling may be achieved by indirect means, for example by separately biotinylating the enzyme and the binding partner using a chemically reactive biotin derivative, (e.g. N-hydroxysuccinimido-biotin, Pierce) and subsequently coupling the molecules through a streptavidin bridging molecule.

Cell based assays are increasingly attractive over in vitro biochemical assays for use in high throughput screening (HTS). This is because cell based assays require minimal manipulation and the readouts can be examined in a biological context that more faithfully mimics the normal physiological situation. Such in vivo assays require an ability to measure a cellular process and a means to measure its output. For example, a change in the pattern of transcription of a number of genes can be induced by cellular signals triggered, for example, by the interaction of an agonist with its cell surface receptor or by internal cellular events such as DNA damage. The induced changes in transcription can be identified by fusing a reporter gene to a promoter region which is known to be responsive to the specific activation signal.

In fluorescence-based enzyme-substrate systems, an increase in fluorescence gives a measure of the activation of the expression of the reporter gene.

Accordingly, in a eighth aspect of the invention, there is provided an assay method which comprises:
i) contacting a host cell which has been transfected with a nucleic acid molecule comprising expression control sequences operably linked to a sequence encoding a nitroreductase, with a dye of formula (I):

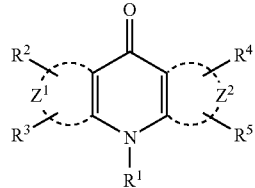

wherein:
groups $R^1$, $R^2$, $R^3$, $R^4$, $R^5$, $Z^1$ and $Z^2$ are hereinbefore defined and wherein at least one of groups $R^1$, $R^2$, $R^3$, $R^4$ and $R^5$ comprises at least one nitro group; and ii) measuring an increase in fluorescence as a measure of nitroreductase gene expression.

In one embodiment of the eighth aspect, the assay method is conducted in the presence of a test agent whose effect on gene expression is to be determined.

Methods for using a variety of enzyme genes as reporter genes in mammalian cells are well known (for review see Naylor L. H., Biochemical Pharmacology, (1999), 58, 749-757). The reporter gene is chosen to allow the product of the gene to be measurable in the presence of other cellular proteins and is introduced into the cell under the control of a chosen regulatory sequence which is responsive to changes in gene expression in the host cell. Typical regulatory sequences include those responsive to hormones, second messengers and other cellular control and signalling factors. For example, agonist binding to seven transmembrane receptors is known to modulate promoter elements including the cAMP responsive element, NF-AT, SRE and AP1; MAP kinase activation leads to modulation of SRE leading to Fos and Jun transcription; DNA damage leads to activation of transcription of DNA repair enzymes and the tumour suppressor gene p53. By selection of an appropriate regulatory sequence the reporter gene can be used to assay the effect of added agents on cellular processes involving the chosen regulatory sequence under study.

For use as a reporter gene, the nitroreductase gene may be isolated by well known methods, for example by amplification from a cDNA library by use of the polymerase chain reaction (PCR) (Molecular Cloning, A Laboratory Manual $2^{nd}$ Edition, Cold Spring Harbour Laboratory Press (1989) pp 14.5-14.20). Once isolated, the nitroreductase gene may be inserted into a vector suitable for use with mammalian promoters (Molecular Cloning, A Laboratory Manual $2^{nd}$ Edition, Cold Spring Harbour Laboratory Press (1989) pp 16.56-16.57) in conjunction with and under the control of the gene regulatory sequence under study. The vector containing the nitroreductase reporter and associated regulatory sequences may then be introduced into the host cell by transfection using well known techniques, for example by use of DEAE-Dextran or Calcium Phosphate (Molecular Cloning, A Laboratory Manual $2^{nd}$ Edition, Cold Spring Harbour Laboratory Press (1989) pp 16.30-16.46). Other suitable techniques will be well known to those skilled in the art.

In another embodiment of the eighth aspect, the dye of formula (I) wherein groups $R^1$, $R^2$, $R^3$, $R^4$, $R^5$, $Z^1$ and $Z^2$ are hereinbefore defined and wherein at least one of groups $R^1$, $R^2$, $R^3$, $R^4$ and $R^5$ comprises at least one nitro group, is permeable to cells. In this embodiment, preferably, at least one of groups $R^1$, $R^2$, $R^3$, $R^4$ or $R^5$ comprises a cell membrane permeabilising group. Membrane permeant compounds can be generated by masking hydrophilic groups to provide more hydrophobic compounds. The masking groups can be designed to be cleaved from the substrate within the cell to generate the derived substrate intracellularly. Because the substrate is more hydrophilic than the membrane permeant derivative it is then trapped in the cell. Suitable cell membrane permeabilising groups may be selected from acetoxymethyl ester which is readily cleaved by endogenous mammalian intracellular esterases (Jansen, A. B. A. and Russell, T. J., J. Chem. Soc., (1965), 2127-2132 and Daehne W. et al. J. Med. Chem., (1970) 13, 697-612) and pivaloyl ester (Madhu et al., J. Ocul. Pharmacol. Ther., (1998), 14(5), 389-399) although other suitable groups will be recognised by those skilled in the art.

Typically, to assay the activity of a test agent to activate cellular responses via the regulatory sequence under study, cells transfected with the nitroreductase reporter are incubated with the test agent, followed by addition of a dye of formula (I) wherein at least one of groups $R^1$, $R^2$, $R^3$, $R^4$ and $R^5$ in said dye comprises at least one nitro group, said compound being made cell permeant. After an appropriate period required for conversion of the substrate to a form exhibiting fluorescence, the fluorescence from the cells is measured at an emission wavelength appropriate for the chosen dye. Measurement of fluorescence may be readily achieved by use of a range of detection instruments including fluorescence microscopes (e.g. LSM 410, Zeiss), microplate readers (e.g. CytoFluor 4000, Perkin Elmer), CCD imaging systems (e.g. LEADseeker™, Amersham Pharmacia Biotech) and Flow Cytometers (e.g. FACScalibur, Becton Dickinson).

The measured fluorescence is compared with fluorescence from control cells not exposed to the test agent and the effects, if any, of the test agent on gene expression modulated through the regulatory sequence, is determined by the detection of the characteristic fluorescence in the test cells. Where appropriate, a cell extract can be prepared using conventional methods.

Suitable means for expressing a nitroreductase enzyme include an expression plasmid or other expression construct. Methods for preparing such expression constructs are well known to those skilled in the art.

In an ninth aspect of the present invention, there is provided a dye of formula (I):

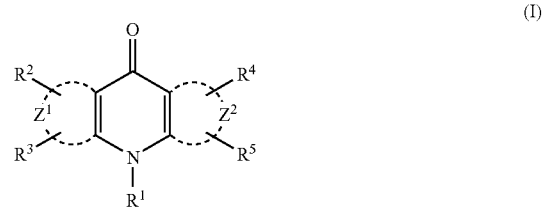

(I)

wherein:
groups $R^2$ and $R^3$ are attached to the $Z^1$ ring structure and groups $R^4$ and $R^5$ are attached to the $Z^2$ ring structure;
$Z^1$ and $Z^2$ independently represent the atoms necessary to complete one ring, two fused ring, or three fused ring aromatic or heteroaromatic systems, each ring having five or six atoms selected from carbon atoms and optionally no more than two atoms selected from oxygen, nitrogen and sulphur;
at least one of groups $R^1$, $R^2$, $R^3$, $R^4$ and $R^5$ is the group -E-F where E is a spacer group having a chain from 1-60 atoms selected from the group consisting of carbon, nitrogen, oxygen, sulphur and phosphorus atoms and F is a target bonding group; and,
when any of said groups $R^1$, $R^2$, $R^3$, $R^4$ and $R^5$ is not said group -E-F, said remaining groups $R^2$, $R^3$, $R^4$ and $R^5$ are independently selected from hydrogen, halogen, amide, hydroxyl, cyano, nitro, amino, mono- or di-$C_1$-$C_4$ alkyl-substituted amino, sulphydryl, carbonyl, carboxyl, $C_1$-$C_6$ alkoxy, acrylate, vinyl, styryl, aryl, heteroaryl, $C_1$-$C_{20}$ alkyl, aralkyl, sulphonate, sulphonic acid, quaternary ammonium and the group —($CH_2$—)$_n$Y; and,
when group $R^1$ is not said group -E-F, it is selected from hydrogen, mono- or di-nitro-substituted benzyl, $C_1$-$C_{20}$ alkyl, aralkyl and the group —($CH_2$—)$_n$Y;
E is a spacer group having a chain from 1-60 atoms selected from the group consisting of carbon, nitrogen, oxygen, sulphur and phosphorus atoms and F is a target bonding group;

Y is selected from sulphonate, sulphate, phosphonate, phosphate, quaternary ammonium and carboxyl; and n is an integer from 1 to 6; provided that at least one of groups $R^1$, $R^2$, $R^3$, $R^4$ and $R^5$ is a water solubilising group.

Preferably, the target bonding group F comprises a reactive group for reacting with a functional group on a target material, or a functional group for reacting with a reactive group on a target material. Preferred reactive groups may be selected from carboxyl, succinimidyl ester, sulpho-succinimidyl ester, isothiocyanate, maleimide, haloacetamide, acid halide, hydrazide, vinylsulphone, dichlorotriazine and phosphoramidite. Preferred functional groups may be selected from hydroxy, amino, sulphydryl, imidazole, carbonyl including aldehyde and ketone, phosphate and thiophosphate.

Preferably, the spacer group E is selected from:

—(CHR')$_p$—

—{(CHR')$_q$—O—(CHR')$_r$}$_s$—

—{(CHR')$_q$—NR'—(CHR')$_r$}$_s$—

—{(CHR')$_q$—(CH=CH)—(CHR')$_r$}$_s$—

—{(CHR')$_q$—Ar—(CHR')$_r$}$_s$—

—{(CHR')$_q$—CO—NR'—(CHR')$_r$}$_s$—

—{(CHR')$_q$—CO—Ar—NR'—(CHR')$_r$}$_s$— where R' is hydrogen, $C_1$-$C_4$ alkyl or aryl, which may be optionally substituted with sulphonate, Ar is phenylene, optionally substituted with sulphonate, p is 1-20, preferably 1-10, q is 0-10, r is 1-10 and s is 1-5.

The dyes of formula (I) may be prepared from the corresponding diphenylamine-2-carboxylic acid according to published methods (see Albert, A. and Ritchie, B.,Org. Syntheses, (1942), 22, 5; also U.S. Pat. No. 3,021,334). Suitably, the diphenylamine-2-carboxylic acid may be heated in the presence of an acidic dehydrating agent such as phosphorus oxychloride or concentrated sulfuric acid. The diphenylamine-2-carboxylic acid derivatives may be prepared by reaction of a 2-halobenzoic acid with a suitable primary aminobenzene (having at least one aryl ring position unsubstituted ortho- to the amino group), which reaction may be performed in the presence of catalytic copper metal/salt (see Ullmann, F., Chem. Ber., (1903), 36, 2382; also British Patent 649147). Suitably, the 2-halobenzoic acid is heated with the aminobenzene, in the presence of a base such as an alkali metal carbonate, in a solvent such as 1-butanol or 1-pentanol. A catalytic amount of copper metal powder or a copper salt such as anhydrous copper acetate is also usually included, although sometimes this is not required.

It will be readily appreciated that certain dyes of the present invention may be useful as intermediates for conversion to other dyes by methods well known to those skilled in the art. The dyes of the present invention may be synthesized by the methods disclosed herein. Derivatives of the compounds having a particular utility are prepared either by selecting appropriate precursors or by modifying the resultant compounds by known methods to include functional groups at a variety of positions. As examples, the dyes of the present invention may be modified to include certain reactive groups for preparing a dye according to the present invention, or charged or polar groups may be added to enhance the solubility of the compound in polar or nonpolar solvents or materials. As examples of conversions, an ester may be converted to a carboxylic acid or may be converted to an amido derivative. Groups $R^1$ to $R^5$ may be chosen so that the dyes of the present invention have different lifetime characteristics, thereby providing a number of related dyes which can be used in multiparameter analyses wherein the presence and quantity of different compounds in a single sample may be differentiated based on the wavelengths and lifetimes of a number of detected fluorescence emissions. The dyes of the present invention may be made soluble in aqueous, other polar, or non-polar media containing the material to be labelled by appropriate selection of R-groups.

Figure 3:
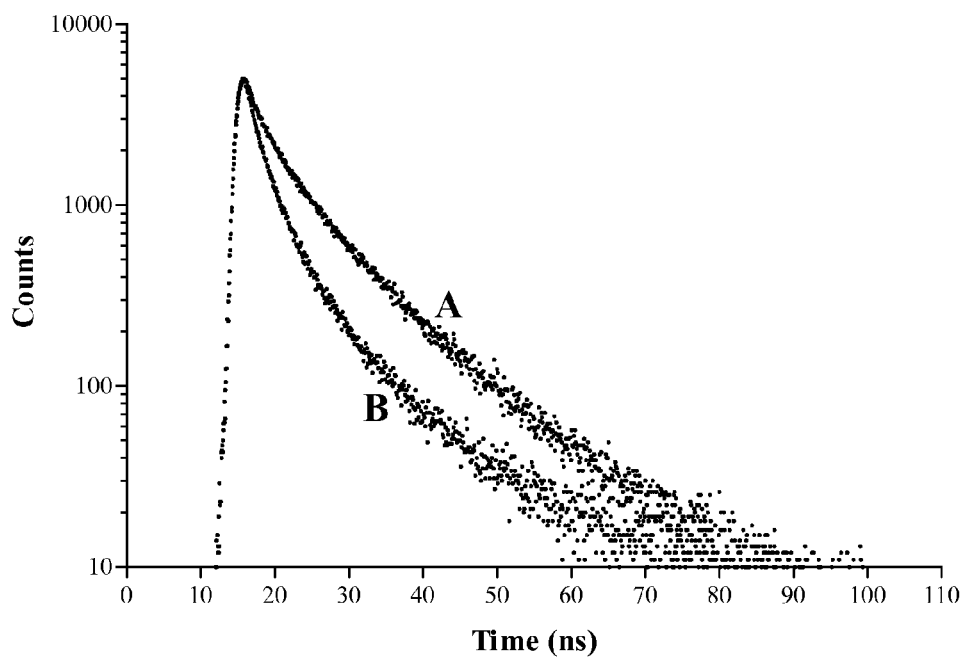
Figure 4:
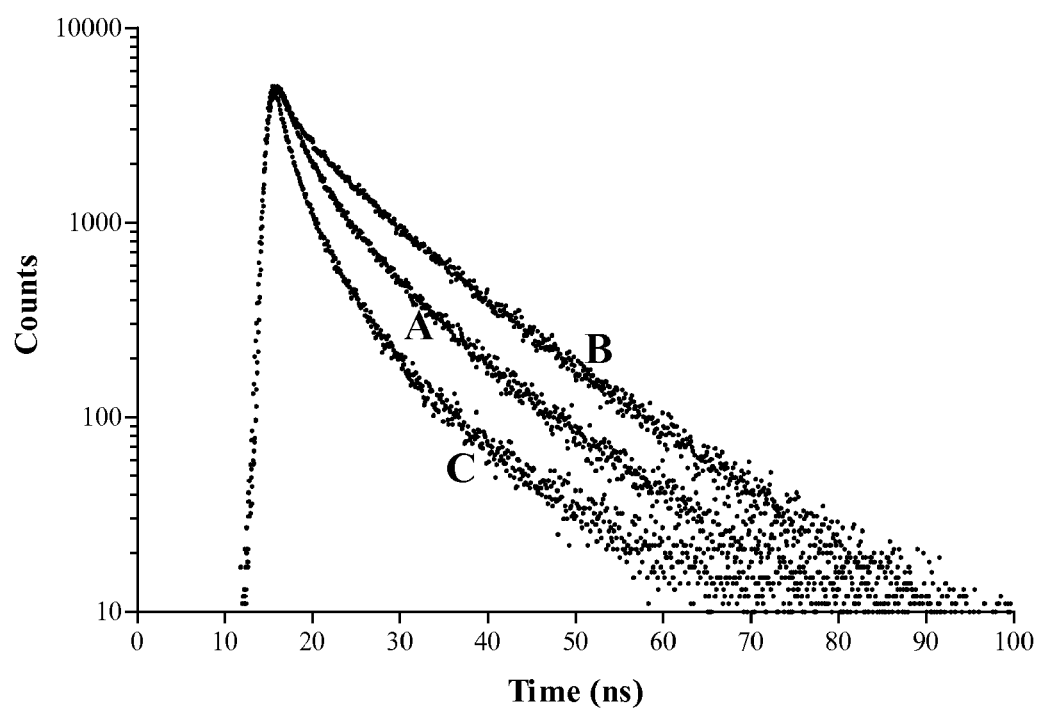
Figure 5:
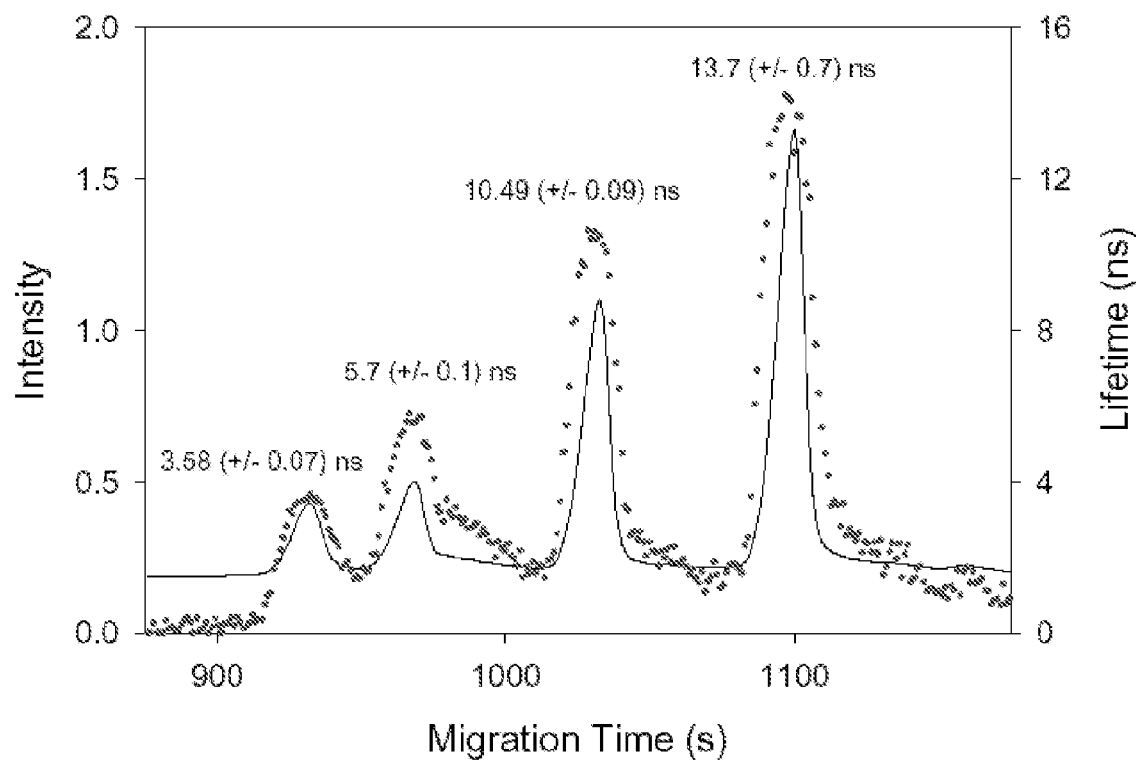
Figure 6:
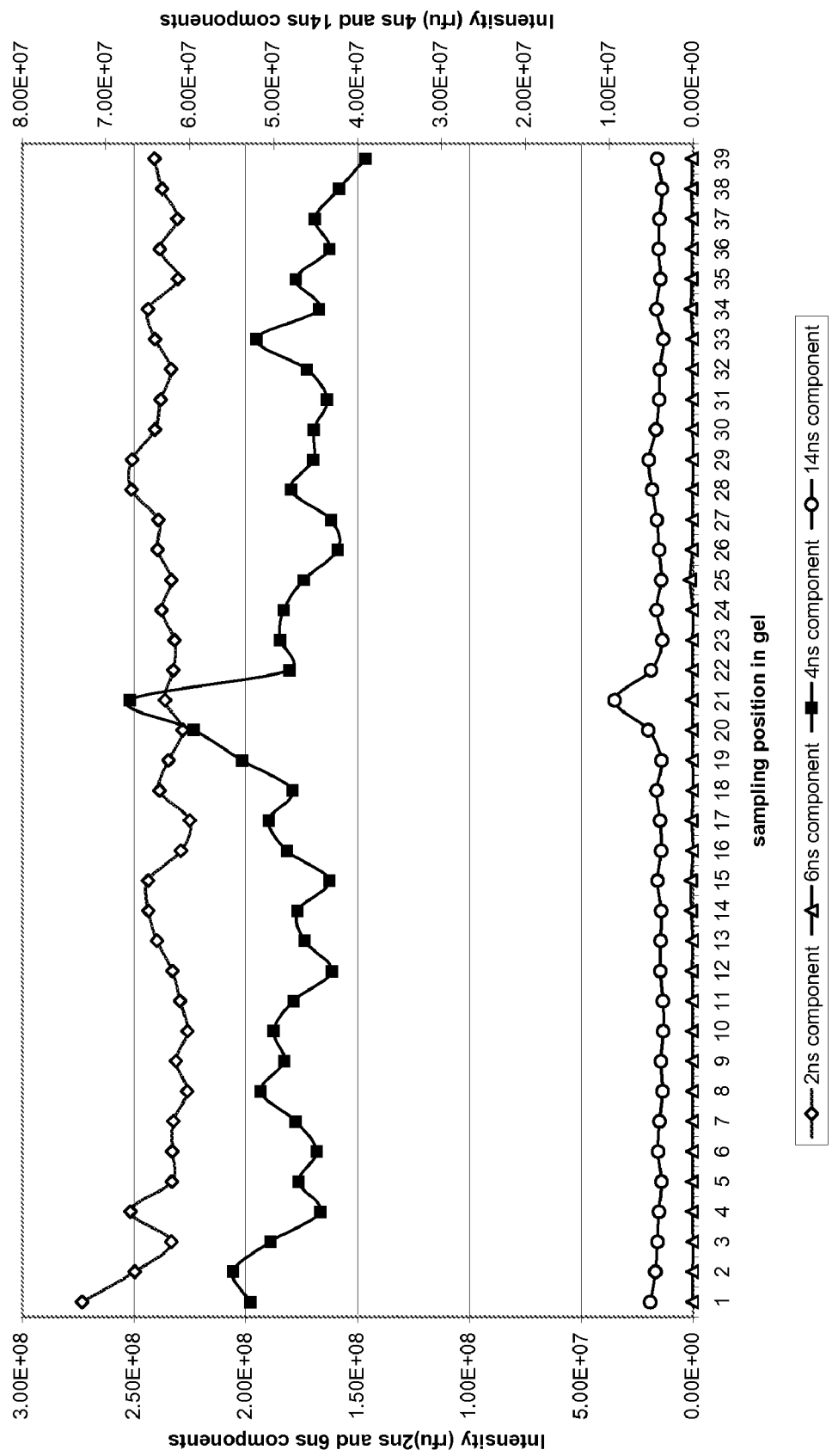

------ : N-(succinyl)-2-amino-10H-acridine-9-one;

●●●●●●: 6-(9-oxo-9H-acridin-10-yl)hexanoic acid;

— — — —:6-(2-bromo-9-oxo-9H-acridin-10-yl)hexanoic acid;

●● — ●● —: 6-(9-oxo-9H-acridin-4-carboxamido) hexanoic acid;

FIG. 3 shows lifetime decay plots of protein conjugates as follows:

Conjugate 1=6-(9-oxo-9H-acridin-10-yl)hexanoic acid-bovine serum albumin (BSA) conjugate; Conjugate 2=6-(9-oxo-9H-acridin-4-carboxamido)hexanoic acid-rabbit serum albumin conjugate;

FIG. 4 is a lifetime decay plot following immunoprecipitation with anti-BSA antibody as described in Example 16;

FIG. 5 illustrates fluorescence lifetime detection in capillary electrophoresis of four acridone dye-labelled DNA fragments as described in Example 17;

FIG. 6 shows the lifetime detection of a mixture of two different acridone dye-labelled BSA conjugates and co-electrophoresed in SDS PAGE as described in Example 19.

Cy™ is a trademark of Amersham Biosciences UK Limited.

EXAMPLES

The present examples are provided for illustrative purposes only, and are not to be construed as limiting the present invention as defined by the appended claims. All references given below and elsewhere in the present specification are hereby included herein by reference.

1. O—(N-Succinimidyl)-6-(9-oxo-9H-acridin-10-yl) hexanoate

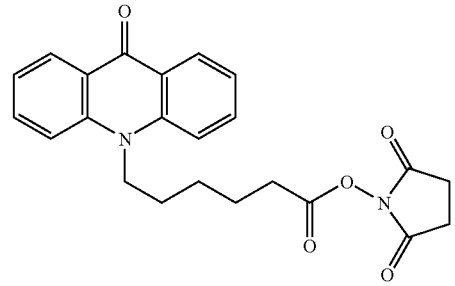

1.1 O-Ethyl-6-(9-oxo-9H-acridin-10-yl)hexanoate 9-(10H)-Acridone (4.88 g, 25 mmol) was mixed with anhydrous methyl sulfoxide (25 ml) under nitrogen atmosphere and set stirring. After 5 minutes, the resultant yellow slurry was treated with potassium tert-butoxide (3.37 g, 30 mmol) and stirring continued until all the solids had dissolved. Ethyl 6-bromohexanoate (6.7 g, 30 mmol) was then added and the resulting solution stirred under nitrogen for 3 days. At the end of this time the reaction mixture was poured into water (1000 ml) and extracted with ethyl acetate. The organic solution was washed with 0.5 M aqueous HCl, then with water, before being dried (MgSO$_4$), filtered and evaporated under vacuum.

The crude product was separated from unreacted acridone by trituration with 1:1 ethyl acetate/hexane; acridone remained undissolved and was filtered off. The filtrate was washed twice with 0.5M aqueous HCl before being dried (MgSO$_4$), filtered and evaporated under vacuum; the acid wash removed most of the O-alkylated acridine side product. The residue was then subjected to flash column chromatography (silica. 30-50% ethyl acetate/hexane) to give 5.9 g (70%) of O-ethyl-6-(9-oxo-9H-acridin-10-yl)hexanoate. This material was finally recrystallized from ethanol (20 ml) to give 5.14 g of analytically pure material. $\lambda_{max}$ (EtOH)=404, 387, 254 nm; $\delta_H$(300 MHz, CD$_3$OD) 1.23 (3H, t), 1.60 (2H, m), 1.73 (2H, m), 1.92 (2H, m), 2.37 (2H, t), 4.11 (2H, q), 4.50 (2H, app.t) 7.34 (2H, m), 7.77 (2H, m), 7.84 (2H, m) and 8.46 (2H, m). Mass spectrum: (ES+) 338 (M+H), 360 (M+Na).

1.2 6-(9-Oxo-9H-acridin-10-yl)hexanoic acid

O-Ethyl-6-(9-oxo-9H-acridin-10-yl)hexanoate (3.40 g, 10 mmol) was mixed with acetic acid (40 ml) and 1.0M aqueous HCl (10 ml). The resulting solution was heated under reflux for 3 hrs until TLC indicated complete conversion to the carboxylic acid (RPC$_{18}$. Methanol, 90: water, 10. R$_f$=0.6). The solution was evaporated under vacuum, then co-evaporated with acetonitrile until a yellow solid was obtained. This was triturated with diethyl ether and dried under high vacuum over phosphorus pentoxide to give 6-(9-oxo-9H-acridin-10-yl)hexanoic acid (3.07 g, 98%). $\lambda_{max}$ (EtOH)=404, 384, 256 nm. $\delta_H$ (300 MHz, CD$_3$OD) 1.62 (2H, m), 1.75 (2H, m), 1.95 (2H, m), 2.36 (2H, t), 4.53 (2H, app.t), 7.35 (2H, m), 7.79 (2H, m), 7.86 (2H, m) and 8.46 (2H, m). Mass spectrum: (ES+) 310 (M+H), 332 (M+Na). Melting Point=167° C.

1.3 O—(N-Succinimidyl)-6-(9-oxo-9H-acridin-10-yl)hexanoate 6-(9-Oxo-9H-acridin-10-yl)hexanoic acid (309 mg, 1.0 mmol) and O—(N-succinimidyl)-N,N,N',N'-tetramethyluronium tetrafluoroborate (TSTU; 301 mg, 1.0 mmol) were dissolved in N,N-dimethylformamide (5 ml). To the resulting solution was added N,N-diisopropylethylamine (183 µl, 1.05 mmol). After 2 hrs the solvent was evaporated under vacuum. The residue was purified by flash chromatography (silica. 0-10% ethyl acetate/dichloromethane) to give O—(N-succinimidyl)-6-(9-oxo-9H-acridin-10-yl)hexanoate as a pale yellow powder (330 mg, 81%). $\delta_H$ (200 MHz, DMSO-d$_6$) 1.63-1.83 (6H, m), 2.74 (2H, t), 2.83 (4H, s), 4.47 (2H, app.t), 7.30-7.38 (2H, m), 7.81-7.84 (4H, m) and 8.34-8.38 (2H, m). Mass spectrum: (ES+) 407 (M+H), 429 (M+Na). Accurate mass: (M+H)=C$_{23}$H$_{23}$N$_2$O$_5$, requires 407.1607. Found 407.1597 (-2.4 ppm).

2. O—(N-Succinimidyl)-6-(2-bromo-9-oxo-9H-acridin-10-yl)hexanoate

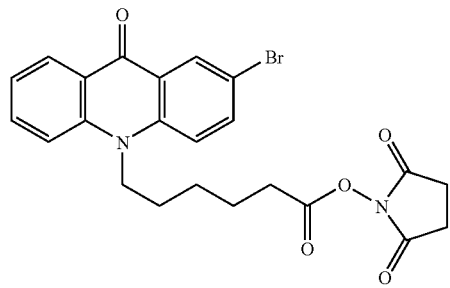

2.1 O-Ethyl-6-(2-bromo-9-oxo-9H-acridin-10-yl)hexanoate and O-ethyl-6-(2,7-dibromo-9-oxo-9H-acridin-10-yl)hexanoate O-Ethyl-6-(9-oxo-9H-acridin-10-yl)hexanoate (4.22 g, 12.5 mmol) was dissolved in ethanol (150 ml) with stirring. To the resulting solution was added benzyltrimethylammoniun tribromide (9.75 g, 25 mmol). The mixture was stirred under nitrogen for 4 days. The solvent was then evaporated under vacuum and the residue partitioned between water (1000 ml) and ethyl acetate (300 ml). The organic layer was collected, washed with more water and dilute aqueous sodium thiosulfate solution, then dried (MgSO$_4$), filtered and evaporated under vacuum.

The crude product was purified by flash column chromatography (silica. 0-5% ethyl acetate/dichloromethane). O-Ethyl-6-(2,7-dibromo-9-oxo-9H-acridin-10-yl)hexanoate eluted first, followed by O-ethyl-6-(2-bromo-9-oxo-9H-acridin-10-yl)hexanoate. Pure fractions of each were pooled and evaporated separately.

O-Ethyl-6-(2-bromo-9-oxo-9H-acridin-10-yl)hexanoate was recrystallized from ethanol. Yield: 2.77 g (53%). $\lambda_{max}$ (EtOH)=412, 392, 300, 278, 256 nm. $\delta_H$(300 MHz, CD$_3$OD) 1.22 (3H, t), 1.58 (2H, m), 1.74 (2H, m), 1.91 (2H, m), 2.37 (2H, t), 4.10 (2H, q), 4.49 (2H, app.t), 7.36 (1H, m), 7.72 (1H, d), 7.78 (1H, d), 7.82-7.92 (2H, m), 8.42 (1H, dd) and 8.52 (1H, dd). Mass spectrum: (ES+) 416 and 418 (M+H), 438 and 440 (M+Na).

O-Ethyl-6-(2,7-dibromo-9-oxo-9H-acridin-10-yl)hexanoate was recrystallized from chloroform/ethanol. Yield: 2.06 g (33%). $\delta_H$ (200 MHz, DMSO-d$_6$) 1.15 (3H, t), 1.50-1.80 (6H, m), 2.31 (2H, t), 4.04 (2H, q), 4.43 (2H, app.t), 7.81 (2H, d), 7.95 (2H, dd) and 8.34 (2H, d).

2.2 6-(2-Bromo-9-oxo-9H-acridin-10-yl)hexanoic acid

O-Ethyl-6-(2-bromo-9-oxo-9H-acridin-10-yl)hexanoate (2.5 g, 6 mmol) was dissolved in acetic acid (30 ml). To this solution was added 1.0M aqueous HCl (10 ml). The mixture was heated under reflux for 3.5 hrs. Reverse phase chromatographic analysis (C$_{18}$) (methanol:water, 90:10) indicated two spots at R$_f$=0.3 and R$_f$=0.55. The solution was then evaporated under vacuum, then co-evaporated with acetonitrile until a yellow solid was obtained. This was triturated with diethyl ether and dried under high vacuum over phosphorus pentoxide to give 6-(2-bromo-9-oxo-9H-acridin-10-yl)hexanoic acid (2.27 g, 97%). $\delta_H$ (200 MHz, DMSO-d$_6$) 1.50-1.65 (4H, m), 1.70-1.81 (2H, m), 2.25 (2H, t), 4.46 (2H, app.t), 7.32-7.40 (1H, m), 7.78-7.98 (4H, m) and 8.31-8.41 (2H, m). $\lambda_{max}$ (EtOH)=414, 397, 256 nm. Melting Point=213° C.

2.3 O—(N-Succinimidyl)-6-(2-bromo-9-oxo-9H-acridin-10-yl)hexanoate 6-(2-Bromo-9-oxo-9H-acridin-10-yl)hexanoic acid (388 mg, 1.0 mmol) and O—(N-succinimidyl)-N,N,N',N'-tetramethyluronium tetrafluoroborate (TSTU; 301 mg, 1.0 mmol) were dissolved in N,N-dimethylformamide (5 ml). To the resulting solution was added N,N-diisopropylethylamine (183 µl, 1.05 mmol). After 2 hrs the solvent was evaporated under vacuum. The residue was purified by flash chromatography (silica. 0-10% ethyl acetate/dichloromethane) to give O—(N-succinimidyl)-6-(2-bromo-9-oxo-9H-acridin-10-yl)hexanoate (330 mg, 87%) $\delta_H$ (200 MHz, DMSO-d$_6$) 1.5-1.8 (6H, m), 2.73 (2H, t), 2.80 (4H, s), 4.47 (2H, app.t), 7.32-7.42 (1H, m), 7.78-7.83 (3H, m), 7.94 (1H, dd), 8.35 (1H, d) and 8.41 (1H, d). Mass spectrum: (ES+) 485+487 (M+H), 507/509 (M+Na). Accurate mass: (M+H)=C$_{23}$H$_{22}$BrN$_2$O$_5$, requires 485.0712. Found 485.0689 (-4.8 ppm).

3. O—(N-Succinimidyl)-6-(2,7-dibromo-9-oxo-9H-acridin-10-yl)hexanoate

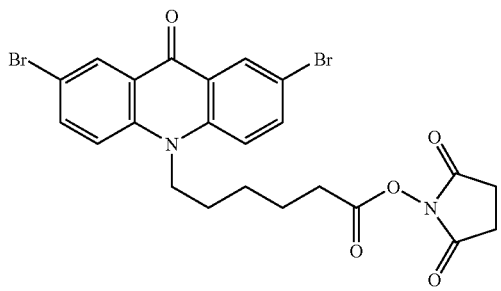

3.1 6-(2,7-Dibromo-9-oxo-9H-acridin-10-yl)hexanoic acid

O-Ethyl-6-(2,7-dibromo-9-oxo-9H-acridin-10-yl)hexanoate (2.0 g, 4.04 mmol) was dissolved in acetic acid (30 ml). To this solution was added 1.0M aqueous HCl (10 ml). The mixture was heated under reflux for 4 hrs. Reverse phase chromatographic analysis ($C_{18}$) (methanol:water, 90:10) indicated two spots at $R_f$=0.2 and $R_f$=0.4. The solution was allowed to cool to ambient temperature, whereupon the product crystallized as fluffy yellow needles. After final cooling in an ice bath, the solid was collected by vacuum filtration, washed with cold aqueous acetic acid, then diethyl ether and dried under vacuum over phosphorus pentoxide to give 6-(2,7-dibromo-9-oxo-9H-acridin-10-yl)hexanoic acid (1.80 g, 97%). $\delta_H$ (200 MHz, DMSO-$d_6$) 1.50-1.80 (6H, m), 2.25 (2H, t), 4.40 (2H, app.t), 7.78 (2H, d), 7.92 (2H, dd) and 8.3 (2H, d).

3.2 O—(N-Succinimidyl)-6-(2,7-dibromo-9-oxo-9H-acridin-10-yl)hexanoate 6-(2,7-Dibromo-9-oxo-9H-acridin-10-yl)hexanoic acid (467 mg, 1.0 mmol) and O—(N-succinimidyl)-N,N,N',N'-tetramethyluronium tetrafluoroborate (TSTU; 301 mg, 1.0 mmol) were dissolved in N,N-dimethylformamide (5 ml). To the resulting solution was added N,N-diisopropylethylamine (183 μl, 1.05 mmol). After leaving to stand overnight, the solvent was evaporated under vacuum. The residue was purified by flash chromatography (silica. 10% ethyl acetate/dichloromethane) to give O—(N-succinimidyl)-6-(2,7-dibromo-9-oxo-9H-acridin-10-yl)hexanoate (510 mg, 91%). $\delta_H$ (200 MHz, DMSO-$d_6$) 1.5-1.8 (6H, m), 2.72 (2H, t), 2.83 (4H, s), 4.44 (2H, app.t), 7.82 (2H, d), 7.95 (2H, dd) and 8.36 (2H, d). Mass spectrum: (ES+) 563+565+567 (M+H), 585+587+589 (M+Na). Accurate mass: (M+Na)=$C_{23}H_{20}Br_2N_2O_5Na$, requires 584.9637. Found 584.9608 (−4.9 ppm).

4. O—(N-Succinimidyl)-6-(9-oxo-9H-acridin-4-carboxamido)hexanoate

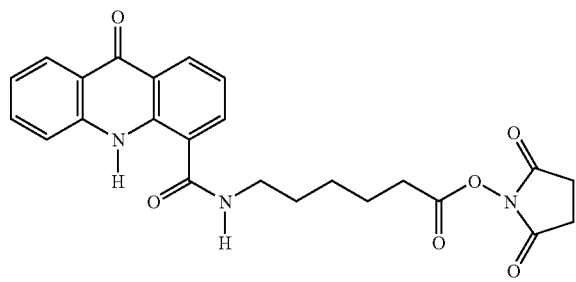

4.1 4-Carboxyacridone 2,2'-Iminodibenzoic acid (5.27 g, 20.5 mmol) was mixed with phosphorus oxychloride (20 ml). The resulting pale yellow slurry was heated to boiling. The slurry turned initially bright yellow, then dissolved to give a deep red solution which was intensely yellow at the meniscus. After 2 hrs at reflux, excess solvent was evaporated under vacuum to give a dark oil. This was quenched with ice, then diluted with 2.0M aqueous HCl (25 ml) and the resulting dark solution re-heated to boiling. After 20 mins a solid precipitated and the mixture became very thick; another 20 mls of water was then added to allow effective stirring. After 1.5 hrs, the mixture was allowed to cool to ambient temperature. The yellow solid was collected by vacuum filtration, washed well with water, then acetone, and dried under vacuum to give 4-carboxyacridone (4.61 g, 94%). $\lambda_{max}$ (EtOH)=408, 390, 256 nm. $\delta_H$ (300 MHz, DMSO-$d_6$) 7.24-7.33 (2H, m), 7.67-7.76 (2H, m), 8.17 (1H, d), 8.38 (1H, dd), 8.47 (1H, dd) and 11.9 (broad s, partially exch). Mass spectrum: (ES+) 240 (M+H), 262 (M+Na). Melting Point>300° C.

4.2 6-(9-Oxo-9H-acridin-4-carboxamido)hexanoic acid

4-Carboxyacridone (2.15 g, 9 mmol), was mixed with N,N-dimethylformamide (15 ml) and N,N-diisopropylethylamine (1.6 ml, 9.2 mmol) and stirred under nitrogen to give a deep yellow solution. To this was added O-benzotriazol-1-yl-N,N,N',N'-tetramethyluronium hexafluorophosphate (3.5 g, 9 mmol) and stirring continued for 2 hrs. During this time a thick yellow precipitate formed. 6-Aminohexanoic acid (1.45 g, 11 mmol) was then added and stirring continued overnight. Reverse phase chromatographic analysis ($C_{18}$) (methanol:water, 80:20) indicated two spots at $R_f$=0.75 and $R_f$=0.55. The reaction mixture was then poured into 0.25M aqueous HCl (200 ml) and the precipitated product collected by vacuum filtration, washing with more dilute HCl and water. The still-damp solid was recrystallized from ethanol/water and dried under vacuum over phosphorus pentoxide to give 6-(9-oxo-9H-acridin-4-carboxamido)hexanoic acid (1.97 g, 62%). $\lambda_{max}$ (EtOH)=408, 390, 256 nm. $\delta_H$ (300 MHz, DMSO-$d_6$) 1.35-1.65 (6H, m), 2.24 (2H, t), 3.40 (2H, t), 7.26-7.39 (2H, m), 7.74-7.77 (2H, m), 8.21-8.28 (2H, m), 8.44 (2H, app.d), 9.00 (1H, broad t, amide), 12.02 (broad s, $D_2O$ exch.) and 12.49 (broad s, $D_2O$ exch.). Mass spectrum: MALDI-TOF, m/z=353.15, M=353.15 for $C_{20}H_{21}N_2O_4$. Melting Point=218° C.

4.3 O—(N-Succinimidyl)-6-(9-oxo-9H-acridin-4-carboxamido)hexanoate 6-(9-Oxo-9H-acridin-4-carbaxamido)hexanoic acid (352 mg, 1.0 mmol) and O—(N-succinimidyl)-N,N,N',N'-tetramethyluronium tetrafluoroborate (TSTU; 301 mg, 1.0 mmol) were dissolved in N,N-dimethylformamide (5 ml). To the resulting solution was added N,N-diisopropylethylamine (183 μl, 1.05 mmol). After leaving to stand overnight the solvent was evaporated under vacuum. The residue was purified by flash chromatography (silica. 10-100% ethyl acetate/dichloromethane) to give O—(N-succinimidyl)-6-(9-oxo-9H-acridin-4-carbaxamido)hexanoate (410 mg, 91%). $\delta_H$ (200 MHz, DMSO-$d_6$) 1.44-1.75 (6H, m), 2.71 (2H, t), 2.79 (4H, s), 3.38 (2H, t), 7.27-7.39 (2H, m), 7.75 (2H, app.d), 8.21-8.28 (2H, m), 8.44 (1H, app.d), 9.00 (1H, broad t, amide) and 12.47 (broad s, $D_2O$ exch.). Mass spectrum: (ES+) 450 (M+H), 472 (M+Na). Accurate mass: (M+H)=$C_{24}H_{24}N_3O_6$, requires 450.1665. Found 450.1671 (+1.3 ppm).

5. 2-Carboxymethyl-7-chloro-9-oxo-9,10-acridine

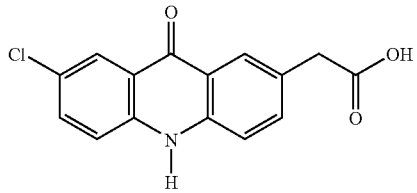

5.1 N-(4-Carboxymethylphenyl)-4-chloro-2-carboxyaniline

To a 100 ml round bottomed flask was added 2,5-dichlorobenzoic acid (1.9 g, 10 mmol), 4-aminophenylacetic acid (1.5 g, 10 mmol), anhydrous sodium carbonate (3.2 g, 26 mmol), activated copper metal powder (0.25 g, 4 mmol) and 1-butanol (50 ml). The flask was fitted with a magnetic stirrer bar, water condenser, silica gel guard tube and heated under reflux for 48 hours. TLC (RPC$_{18}$, Water, 20: methanol, 80) showed the formation of a slower moving component at R$_f$ 0.55. The solvent was removed under reduced pressure with final drying under high vacuum. The residue was dissolved in 50 ml water and heated to boiling, then charcoal was added and the mixture filtered through celite, washing through with a further 25 ml of hot water. This solution was cooled to 10° C. in an ice bath and then acidified to pH≈2 with concentrated aqueous HCl. The oil that separated was extracted into chloroform, the solution dried with anhydrous magnesium sulphate, filtered and the solvent removed by rotary evaporation to leave a sticky solid. Recrystallization from water/acetic acid gave the title compound (1.07 g, 35%). δ$_H$ (300 MHz, DMSO-d$_6$) 3.54 (2H, s), 7.15-7.27 (5H, m), 7.39 (1H, dd) 7.81 (1H, d), 9.54 (1H, broad s) and 12.0-13.5 (2H, broad). Mass spectrum: (ES−) 304 (M−H). λ$_{max}$ (EtOH)=292, 364 nm.

5.2 2-Carboxymethyl-7-chloro-9-oxo-9,10-acridine

To a 25 ml round bottomed flask was added the diphenylamine (500 mg, 1.64 mmol) and phosphorus oxychloride (5 ml). The flask was fitted with a magnetic stirrer bar, water condenser, silica gel guard tube and heated under reflux for 1 hour. The excess phosphorus oxychloride was removed from the dark brown mixture under vacuum, then a small amount of ice was added followed by 2.0M aqueous HCl (10 ml). The mixture was heated to 100° C. for 1 hour and allowed to cool, before being evaporated to dryness and dried under vacuum over phosphorus pentoxide. The residue was dissolved in 10% v/v water/methanol and eluted through a SepPak RPC$_{18}$ (10 g) column with monitoring by TLC. The fluorescence-containing fractions were combined, evaporated to dryness and dried under vacuum over phosphorus pentoxide.

This semi-purified material was then further purified by preparative HPLC (RPC$_{18}$. Water→methanol gradient). Pure fractions were combined and evaporated to give 2-carboxymethyl-7-chloro-9-oxo-9,10-acridine as a pale yellow solid (19 mg, 4%). δ$_H$ (300 MHz, DMSO-d$_6$) 3.72 (2H, s), 7.50 (1H, m), 7.58 (1H, m), 7.65 (1H, m), 7.75 (1H, m), 8.10 (1H, m), 8.14 (1H, m) and 11.9+12.4 (2× broad s). Mass spectrum: (ES−) 286+288 (M−H), 242+244 (M−H—CO$_2$). λ$_{max}$ (EtOH)=260, 390, 408 nm.

6. N-(Succinyl)-2-amino-10H-acridine-9-one

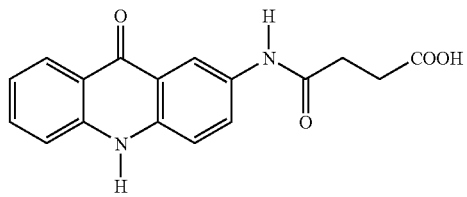

2-Amino-10H-acridine-9-one (100 mg, 0.48 mM), succinic anhydride (50 mg, 0.5 Mm), diisopropylethylamine (90 μl) and dry DMF (1 ml) were stirred together overnight. TLC(C-18 reverse phase plates, water:methanol 1:1) indicated that all the starting material (green fluorescence under long wavelength UV light) had been converted to a faster running spot, which showed blue fluorescence under long wavelength UV light. The solvent was removed by rotary evaporation, the residue dissolved in dichloromethane and purified by flash column chromatography (silica, 0-10% methanol/dichloromethane). Pure fractions of each were pooled and evaporated to dryness to give N-(succinyl)-2-amino-10H-acridine-9-one, 147 mg (98%). λ$_{max}$ (H$_2$O)=399 nm. δ$_H$ (300 MHz, d$_6$-DMSO) 2.05 (4H, m), 6.82 (1H, t), 7.15 (2H, m), 7.28 (1H, t), 7.53 (1H, d), 7.81 (1H, d), 8.09 (1H, s). Mass spectrum: (ES+) 311. M.Pt>300° C.

7. 2-Nitroacridone-7-sulphonic acid

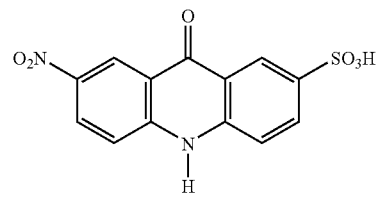

7.1 2-Carboxy-4-nitrodiphenylamine

2-Chloro-5-nitrobenzoic acid (15 g, 75 mmol) was mixed with 1-butanol (100 ml) and stirred. To the resulting mixture was added aniline (15 ml, 15.3 g, 165 mmol) and N,N-diisopropylethylamine (28.8 ml, 21.3 g, 165 mmol). The resulting light yellow solution was heated under reflux for 4 days, during which time the colour changed to deep yellow. TLC (RPC$_{18}$, Methanol, 80: water, 20. R$_f$=0.75, yellow: R$_f$ 2-chloro-5-nitrobenzoic acid=0.85).

The solvent was evaporated under vacuum as much as possible. The residual oil was triturated with water acidified with aqueous HCl to maintain a pH of 2-4. A yellow solid eventually separated. This was collected by vacuum filtration, washed well with excess water and allowed to suck dry over 15 minutes. The crude product was purified by mixing with acetic acid (150 ml), then heating to boiling and allowing the resulting mixture to cool slowly to ambient temperature with stirring. The bright yellow solid so obtained was collected by vacuum filtration, washed with acetic acid followed by excess diethyl ether and dried under vacuum over phosphorus pentoxide to give 2-carboxy-4-nitro-diphenylamine (12.02 g, 62%). $\delta_H$ (200 MHz, DMSO-$d_6$) 7.14 (1H, d), 7.24-7.52 (5H, m), 8.18 (1H, dd), 8.72 (1H, d) and 10.38 (1H, broad s).

7.2 2-Nitroacridone

2-Carboxy-4-nitrodiphenylamine (5.16 g, 20 mmol) was mixed with phosphorus oxychloride (20 ml). The resulting yellow slurry was heated under reflux for 3 hrs, during which time the solids dissolved to give a dark solution (intensely yellow at the meniscus). The excess phosphorus oxychloride was then evaporated under vacuum; the resulting oil was carefully quenched with ice before addition of 1.0M aqueous HCl (100 ml). The mixture was then heated to boiling, whereupon acetic acid (up to 20 ml) was slowly added down the condenser to aid dispersion of the immiscible oil. On continued boiling for 1 hour, a yellow slurry resulted. After subsequent cooling, this solid was collected by vacuum filtration, washed with excess water, then acetone and finally diethyl ether, before drying under vacuum over phosphorus pentoxide to give 2-nitroacridone (4.66 g, 97%). $\delta_H$ (200 MHz, DMSO-$d_6$) 7.39 (1H, app.t), 7.60 (1H, d), 7.68 (1H, d), 7.84 (1H, app.t), 8.25 (1H, d), 8.48 (1H, dd), 8.98 (1H, d) and 12 38 (1H, broad s).

7.3 2-Nitroacridone-7-sulphonic acid

2-Nitroacridone (25 mg) was mixed with fuming sulphuric acid (~20% free $SO_3$, 2.5 ml) to give a reddish solution. This was heated at 100° C. for 90 mins, to give a yellowish solution. After cooling, the mixture was quenched dropwise into ice (~15 g); 6 ml of concentrated HCl were added and the mixture left to stand to precipitate out the product. The resulting pale yellow solid was collected by vacuum filtration, washed with a little 4.0M aqueous HCl, then redissolved in water and filtered into a clean flask. The water was evaporated under vacuum to leave 2-nitroacridone-7-sulphonic acid as a yellow-brown solid. TLC acid ($RPC_{18}$, Methanol, 80: water, 20. $R_f$=0.8, yellow. Mass spectrum: (ES+) 321 (M+H); accurate mass: (M+H)=$C_{13}H_9N_2O_6S$ requires 321.0181. Found 321.0187 (1.8 ppm).

8. O—(N-Succinimidyl)-6-(2-acetamido)-9-oxo-9H-acridin-10-yl)hexanoate

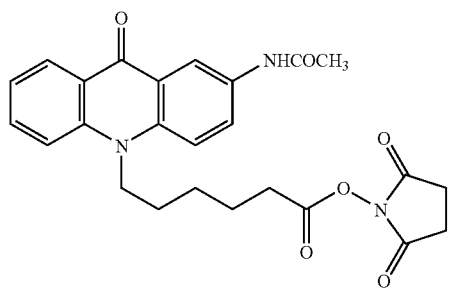

8.1 O-Ethyl-6-(2-nitro-9-oxo-9H-acridin-10-yl)hexanoate

2-Nitroacridone (2.4 g; 10 mmol) was stirred with anhydrous methyl sulphoxide (25 ml) under a nitrogen atmosphere. After 5 minutes, sodium hydride (60% dispersed in oil, 480 mg; 12 mmol) was added to the yellow solution. Stirring was continued for 90 mins. during which time the solution turned magenta. Ethyl 6-bromohexanoate (2.67 ml; 12 mmol) was added and stirring continued overnight. The reaction mixture was poured into water (300 ml) and the yellow precipitate was collected by filtration, washed with water and dried under vacuum. The solid was dissolved in dichloromethane and anhydrous magnesium sulphate added to the solution. After filtration, the solution was evaporated to dryness to leave a yellow-brown solid. The crude product was purified by flash chromatography (silica. 0-5% ethyl acetate/dichloromethane) to give 1.19 g (50%) of O-ethyl-6-(2-nitro-9-oxo-9H-acridin-10-yl)hexanoate.

$\delta_H$ (200 MHz, DMSO-$d_6$) 1.2 (3H, t), 1.7 (6H, m), 2.3 (2H, t), 4.05 (2H, q), 4.55 (2H, m), 7.45 (1H, m), 7.92 (2H, d), 8.03 (1H, d), 8.35 (1H, d), 8.50 (1H, dd), 9.03 (1H, d).

8.2 O-Ethyl-6-(2-amino-9-oxo-9H-acridin-10-yl) hexanoate

O-Ethyl-6-(2-nitro-9-oxo-9H-acridin-10-yl)hexanoate (1.91 g; 5.0 mmol) and ammonium formate (1.58 g; 25 mmol) were dissolved in ethanol (100 ml) to give a yellow solution. The solution was stirred under nitrogen and a catalytic amount of 5% palladium on carbon was added. Stirring was continued for 5 hrs. The solution was then filtered through celite and the solvent removed by rotary evaporation. The residue was dissolved in dichloromethane and extracted with water. The organic layer was dried with anhydrous magnesium sulphate, filtered and the solvent removed by rotary evaporation. The crude product was purified by flash chromatography (silica. 4-6% methanol/dichloromethane) to give 1.66 g (94%) of O-ethyl-6-(2-amino-9-oxo-9H-acridin-10-yl)hexanoate.

$\delta_H$ (200 MHz, DMSO-$d_6$) 1.15 (3H, t), 1.6 (6H, m), 2.35 (2H, t), 4.05 (2H, dd), 4.4 (2H, t), 5.3 (2H, s), 7.2 (2H, m), 7.6 (4H, m), 8.3 (1H, d).

8.3 6-(2-Amino-9-oxo-9H-acridin-10-yl)hexanoic acid

O-Ethyl-6-(2-amino-9-oxo-9H-acridin-10-yl)hexanoate (350 mg; 1.0 mmol) was dissolved in acetic acid (5 ml) and 1.0M hydrochloric acid (2 ml) and refluxed for 4 hrs. The solvent was removed by rotary evaporation, the residue dissolved in acetic acid and evaporated to dryness and the process repeated twice using acetonitrile as solvent. The residue was dried under vacuum to give 370 mg of 6-(2-amino-9-oxo-9H-acridin-10-yl)hexanoic acid.

8.4 6-(2-Acetamido-9-oxo-9H-acridin-10-yl)hexanoic acid 6-(2-Amino-9-oxo-9H-acridin-10-yl)hexanoic acid (370 mg: 1.14 mmol) was dissolved in anhydrous pyridine (10 ml) and acetic anhydride (100 µl) followed by diisopropylethylamine (350 µl). The mixture was stirred for 3 hours. The solution was evaporated to dryness under vacuum and the gummy residue dissolved in dichloromethane. The solution was washed with 1.0M hydrochloric acid and then brine. The organic phase was dried with anhydrous magnesium sulphate, filtered and the solvent removed by rotary evaporation to leave a sticky solid. Trituration with ether gave a solid which was dried under vacuum to give 360 mg (86%) of 6-(2-acetamido-9-oxo-9H-acridin-10-yl)hexanoic acid.

8.5 O—(N-Succinimidyl)-6-(2-acetamido-9-oxo-9H-acridin-10-yl)hexanoate 6-(2-Acetamido-9-oxo-9H-acridin-10-yl)hexanoic acid (360 mg; 1.0 mmol) and O—(N-succinimidyl)-N,N,N',N'-tetramethyluronium tetrafluoroborate (350 mg; 1.0 mmol) were dissolved in anhydrous dimethylformamide (5 ml) and diisopropylethylamine (183 µl) added. The yellow solution was stirred under nitrogen for 1 hour. The solvent was removed by rotary evaporation to leave a brown gum. This was purified by flash chromatography (silica. 10% methanol/ethyl acetate) to give 330 mg (50%) of O—(N-succinimidyl)-6-(2-acetamido-9-oxo-9H-acridin-10-yl)hexanoate. $\delta_H$ (200 MHz, DMSO-$d_6$) 1.8 (6H, m), 2.1 (3H, s), 2.9 (6H, m), 4.5 (2H, m), 7.3 (1H, m), 7.8 (3H, m), 8.05 (1H, d), 8.35 (1H, d), 8.6 (1H, s), 10.2 (1H, s). Accurate mass. (M+H) =$C_{25}H_{26}N_3O_6$, requires 464.1822. Found 464.1798 (5.1 ppm).

9. O—(N-Succinimidyl)-6-(2-sulpho-9-oxo-9H-acridin-10-yl)hexanoate

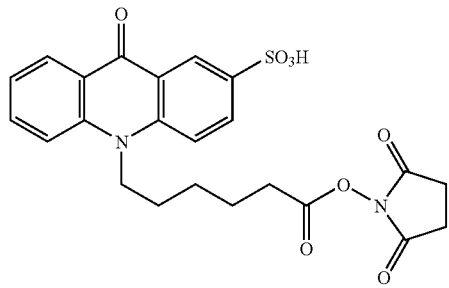

9.1 6-(2-Sulpho-9-oxo-9H-acridin-10-yl)hexanoic acid

O-Ethyl-6-(9-oxo-9H-acridin-10-yl)hexanoate (2.0 g; 6.0 mmol) was dissolved in conc. sulphuric acid (10 ml) and the solution heated to 120° C. for 20 hrs. The mixture was allowed to cool and added to ~50 gm of crushed ice. The precipitate was collected by centrifugation, washed with 3.0M hydrochloric acid and dried under vacuum and over phosphorous pentoxide to give 2.1 g (90%) of 6-(2-sulpho-9-oxo-9H-acridin-10-yl)hexanoic acid. $\delta_H$ (200 MHz, DMSO-$d_6$) 1.7 (6H, m), 2.26 (2H, t), 4.5 (2H, t), 7.37 (1H, m), 7.9 (5H, m), 8.37 (1H, d), 8.58 (1H, d). Mass spectrum: (ES+) (M+H) 390.

9.2 O—(N-Succinimidyl)-6-(2-sulpho-9-oxo-9H-acridin-10-yl)hexanoate 6-(2-Sulpho-9-oxo-9H-acridin-10-yl)hexanoic acid (100 mg; 0.25 mmol) was dissolved in anhydrous dimethylformamide (3 ml) and evaporated to dryness on a rotary evaporator. The process was repeated to remove traces of water. O—(N-Succinimidyl)-N,N,N',N'-tetramethyluronium tetrafluoroborate (90 mg; 0.3 mmol) was added and the mixture dissolved in anhydrous dimethylformamide (2 ml) and diisopropylethylamine (90 µl). The yellow solution was stirred under nitrogen for 60 mins when TLC(RP$_{18}$ 50:50 water:methanol) showed all the starting material had been converted to a slower moving component. The solvent was removed by rotary evaporation with final drying under high vacuum. No further attempts were made to purify this material.

10. 6-(2-Bromo-7-sulpho-9-oxo-9H-acridin-10-yl)hexanoic acid

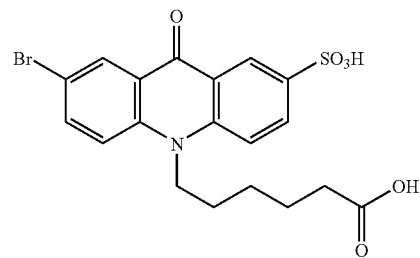

O-ethyl-6-(2-bromo-9-oxo-9H-acridin-10-yl)hexanoate (2.08 gm; 5.0 mmol) was dissolved in conc. sulphuric acid (10 ml) and heated to 120° C. for 20 hrs. The mixture was allowed to cool and added to ~50 gm of crushed ice. The precipitate was collected by centrifugation, washed with 3.0M hydrochloric acid and dried under vacuum in the presence of phosphorous pentoxide to give 2.2 g (94%) of 6-(2-bromo-7-sulpho-9-oxo-9H-acridin-10-yl)hexanoic acid. $\delta_H$ (200 MHz, DMSO-$d_6$) 1.7 (6H, m), 2.25 (2H, t), 4.5 (2H, m), 7.9 (4H, m), 8.42 (1H, d), 8.57 (1H, d). Mass spectrum (ES+) (M+H) 468, 470.

11. N-(Maleimido)ethyl-6-(9-oxo-9H-acridin-10-yl)hexanamide

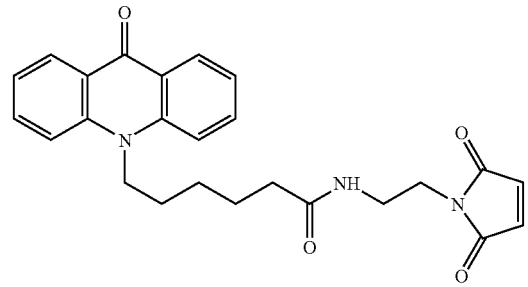

11.1 N-(Aminoethyl)maleimide hydrochloride

N-Butoxycarbonyl-2-(aminoethyl)maleimide (200 mg; 0.83 mmol) was stirred under nitrogen with 4M hydrochloric acid in dioxan (4 ml). A white precipitate started to form after a few minutes. Stirring was continued for 40 minutes and then the solvent was removed by rotary evaporation. The resultant white solid was dried under vacuum to give 180 mg (100%) of N-(aminoethyl)maleimide hydrochloride. $\delta_H$ (200 MHz, CD$_3$OD) 1.38 (2H, s), 3.14 (2H, t), 3.81 (2H, t), 6.90 (2H, s).

11.2 N-(Maleimido)ethyl-6-(9-oxo-9H-acridin-10-yl)hexanamide

O—(N-Succinimidyl)-6-(9-oxo-9H-acridin-10-yl)hexanoate (102 mg; 0.25 mmol) was dissolved in anhydrous dimethyl formamide (800 μl) and diisopropylethylamine (53 μl) added. N-(Aminoethyl)maleimide hydrochloride (53 mg; 0.30 mmol) was added to the yellow solution which was left to stand overnight. The solvent was removed by rotary evaporation and the residue purified by flash chromatography (silica. 2% methanol/dichloromethane). After removal of the solvent by rotary evaporation a yellow oil remained which slowly crystallised. Trituration with diethyl ether completed the crystallisation. This material was further purified by preparative TLC (silica. 5% methanol/dichloromethane) extracting the required material with 10% methanol/dichloromethane.

Solvent was removed under vacuum, the residue triturated with ether to give 65 mg (60%) of N-(maleimido)ethyl-6-(9-oxo-9H-acridin-10-yl)hexanamide. $\delta_H$ (200 MHz, DMSO-$d_6$) 1.7 (6H, m), 2.02 (2H, t), 3.2 (2H, dd), 3.45 (2H, t), 4.45 (2H, t), 7.01 (2H, s), 7.35 (2H, m), 7.85 (5H, m), 8.36 (2H, d). Mass spectrum (ES+) (M+H) 432.

12. N-(Maleimido)ethyl-6-(2-sulpho-9-oxo-9H-acridin-10-yl)hexanamide

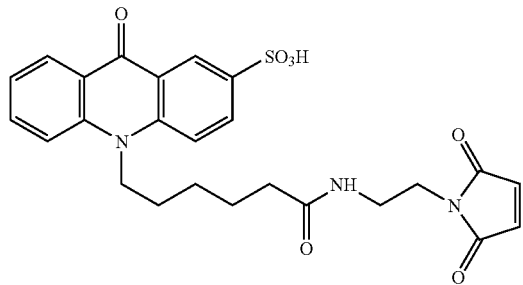

O—(N-Succinimidyl)-6-(2-sulpho-9-oxo-9H-acridin-10-yl)hexanoate (90 mg; 0.15 mmol) was dissolved in anhydrous dimethyl formamide (1.0 ml) and diisopropylethylamine (52 μl) added. N-(aminoethyl)maleimide hydrochloride (52 mg; 0.30 mmol) was added to the yellow solution which was left to stand overnight. The solvent was removed by rotary evaporation and the residue purified by HPLC (Vydac $RP_{18}$ semi-preparative column, gradient of water to 25% acetonitrile (both containing 0.1% trifluoroacetic acid) over 30 minutes, detection at 400 nm) to give N-(maleimido)ethyl-6-(2-sulpho-9-oxo-9H-acridin-10-yl)hexanamide.

13. 6-(2-Fluoro-9-oxo-9H-acridin-10-yl)hexanoic acid

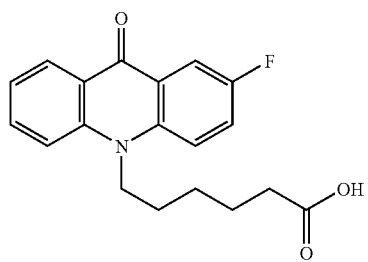

13.1 N-(4-Fluorophenyl)anthranilic acid

4-Fluoroaniline (1.86 gm; 20 mmol), 2-chlorobenzoic acid (1.56 gm; 10 mmol), ethylene glycol (5 ml) and anhydrous sodium carbonate (1.1 gm; 10 mmol) were placed in a reaction vessel and stirred until effervescence ceased. Cupric chloride (100 mg; 0.75 mmol) dissolved in 2 ml of water was added to the reaction mixture which was then heated to 125° C. for 6 hrs. The reaction was allowed to cool and water (30 ml) and charcoal were added. The mixture was filtered and then acidified to pH 2 with conc. hydrochloric acid. The precipitate was collected by filtration, washed with water and then re-dissolved in 1M sodium hydroxide solution. Material was re-precipitated by the addition of acetic acid, filtered off, washed with aqueous acetic acid, then water and finally dried under vacuum over phosphorous pentoxide to give 862 mg (37%) of N-(4-fluorophenyl)anthranilic acid.

13.2 2-Fluoroacridone

N-(4-Fluorophenyl)anthranilic acid (0.70 gm; 3 mmol) and phosphorous oxychloride (3 ml) were stirred together and heated to 115° C. for 3.5 hours, then allowed to cool. The reaction mixture was placed on ice and small pieces of ice added, a vigorous reaction occurred with the evolution of hydrogen chloride. When the reaction had subsided, water (15 ml) was added and the mixture was boiled for 2 hours. On cooling, a solid precipitated out. This was filtered off and washed with water until the filtrate was colourless. The precipitate was further washed with cold methanol then diethyl ether and dried under vacuum to give 383 mg (59%) of 2-fluoroacridone.

13.3 O-Ethyl-6-(2-fluoro-9-oxo-9H-acridin-10-yl)hexanoate

2-Fluoroacridone (213 mg; 1.0 mmol) was dissolved in anhydrous DMF (3 ml) under a nitrogen atmosphere. Sodium hydride dispersed in oil (45 mg; 1.1 mmol) was added and the mixture stirred until effervescence ceased. Ethyl 6-bromoacetate (250 μl) was added and the mixture stirred at 70° C. overnight. The solvent was removed by rotary evaporation and the yellow residue purified by flash chromatography (silica. 4% ethyl acetate/dichloromethane) to give 230 mg (65%) of O-ethyl-6-(2-fluoro-9-oxo-9H-acridin-10-yl)hexanoate. $\delta_H$ (200 MHz, DMSO-$d_6$) 1.20 (3H, t), 1.65 (6H, m), 2.35 (2H, t), 4.05 (2H, dd), 4.45 (2H, t), 7.35 (1H, m), 7.9 (5H, m), 8.35 (1H, d). Mass spectrum (ES+) (M+H) 356.1

13.4 6-(2-Fluoro-9-oxo-9H-acridin-10-yl)hexanoic acid

O-Ethyl-6-(2-fluoro-9-oxo-9H-acridin-10-yl)hexanoate (71 mg; 0.2 mmol) was dissolved in ethanol (2 ml) and 1.0M sodium hydroxide solution (0.4 ml) added and the mixture heated to 90° C. for 90 minutes. The mixture was cooled and water (6 ml) added to give a yellow precipitate. The mixture was cooled on ice and acidified with conc. hydrochloric acid when more material precipitated out. The precipitate was filtered off, washed with water then ethanol and dried under vacuum over phosphorous pentoxide to give 47 mg (72%) of 6-(2-fluoro-9-oxo-9H-acridin-10-yl)hexanoic acid. $\delta_H$ (200 MHz, DMSO-$d_6$) 1.68 (6H, m), 2.25 (2H, t), 4.48 (2H, t), 7.36 (1H, m), 7.85 (5H, m), 8.34 (1H, d).

$\lambda_{max}$(ab) 251 nm ($\epsilon$=45,500/M$^{-1}$ cm$^{-1}$); 401 nm ($\epsilon$=7980/M$^{-1}$ cm$^{-1}$); 421 nm ($\epsilon$=7980/M$^{-1}$ cm$^{-1}$). (PBS buffer). $\lambda_{max}$ (em) 434 nm (PBS buffer).

14. 6-(2-Methoxy-9-oxo-9H-acridin-10-yl)hexanoic acid

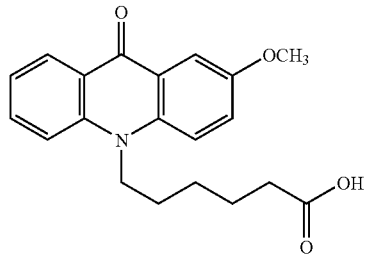

14.1 N-(4-Methoxyphenyl)anthranilic acid

4-Methoxyaniline (1.86 gm; 20 mmol), 2-chlorobenzoic acid (1.56 gm; 10 mmol), ethylene glycol (5 ml) and anhydrous sodium carbonate (1.1 gm; 10 mmol) were placed in a reaction vessel and stirred until effervescence ceased. Cupric chloride (100 mg; 0.75 mmol) dissolved in 2 ml of water was added to the reaction mixture which was then heated to 125° C. for 6 hours. The reaction was allowed to cool then water (30 ml) and charcoal were added. The mixture was filtered and acidified to pH 2 with conc. hydrochloric acid. The precipitate was collected by filtration, washed with water and then re-dissolved in 1M sodium hydroxide solution. Material was re-precipitated by the addition of acetic acid, filtered off, washed with aqueous acetic acid, then water and finally dried under vacuum over phosphorous pentoxide to give 1200 mg (49%) of N-(4-methoxyphenyl)anthranilic acid.

Mass spectrum (ES+) (M+H) 242

14.2 2-Methoxyacridone

Polyphosphoric acid (50 gm) was heated to 160° C. under a nitrogen atmosphere. N-(4-methoxyphenyl)anthranilic acid (4.89 gm; 20 mmol) was added and the mixture stirred at 160° C. for 15 minutes. The reaction was cooled rapidly in an ice bath and water added to give a greenish yellow precipitate. This was filtered off, washed with water, then dilute sodium bicarbonate solution and again with water. The solid was finally dried at 50° C. under vacuum to give 3.67 gm (81%) of 2-methoxyacridone. $\delta_H$ (200 MHz, DMSO-d$_6$) 3.86 (3H, s), 7.23 (1H, t), 7.55 (5H, m), 8.22 (1H, d), 11.7 (1H, s).

14.3 O-Ethyl-6-(2-methoxy-9-oxo-9H-acridin-10-yl)hexanoate

2-Methoxyacridone (2.25 g; 10 mmol) was stirred with anhydrous dimethyl formamide (15 ml) under a nitrogen atmosphere. After 5 minutes, sodium hydride (60% dispersed in oil, 250 mg; 12 mmol) was added and the mixture stirred until effervescence ceased. A second lot of sodium hydride (230 mg) was added and stirring continued until effervescence ceased. Ethyl 6-bromohexanoate (2.67 ml; 15 mmol) was added to the yellow solution and stirring was continued overnight. The reaction mixture was poured into water (300 ml) and the mixture extracted with dichloromethane. The organic phase was washed with 1.0M hydrochloric acid (2×150 ml) then dried over anhydrous magnesium sulphate. After filtration, the solvent was removed by rotary evaporation to give a dark coloured oil. This was purified by flash chromatography (silica. 5% ethanol/dichloromethane) to give a yellow oil which crystallised on trituration with diethyl ether/hexane to give 0.83 g (23%) of 0-ethyl-6-(2-methoxy-9-oxo-9H-acridin-10-yl)hexanoate.

Mass spectrum (ES+) (M+H) 367 (M+Na) 389.

14.4 6-(2-Methoxy-9-oxo-9H-acridin-10-yl)hexanoic acid

O-Ethyl-6-(2-methoxy-9-oxo-9H-acridin-10-yl)hexanoate (367 mg; 1.0 mmol) was dissolved in ethanol (10 ml) and 1.0M sodium hydroxide solution (2.0 ml) added and the mixture heated to 90° C. for 1 hour. The mixture was cooled and water (20 ml) added. The mixture was cooled on ice and acidified with conc. hydrochloric acid when a yellow oil separated. The oil slowly crystallised to a bright yellow solid. This was filtered off, washed with water and dried under vacuum to give 327 mg (96%) of 6-(2-methoxy-9-oxo-9H-acridin-10-yl)hexanoic acid. $\delta_H$ (200 MHz, DMSO-d$_6$) 1.7 (6H, m), 2.25 (2H, t), 3.9 (3H, s), 4.5 (2H, t), 7.31 (1H, m), 7.48 (1H, dd), 7.82 (4H, m), 8.35 (1H, d).

$\lambda_{max}$(ab) 255 nm ($\epsilon$=38,100/M$^{-1}$ cm$^{-1}$); 408 nm ($\epsilon$=7150/M$^{-1}$ cm$^{-1}$); 428 nm ($\epsilon$=7150/M$^{-1}$ cm$^{-1}$). (PBS buffer). $\lambda_{max}$ (em) 467 nm. (PBS buffer).

15. Fluorescence Lifetime Studies

Figure 1A:
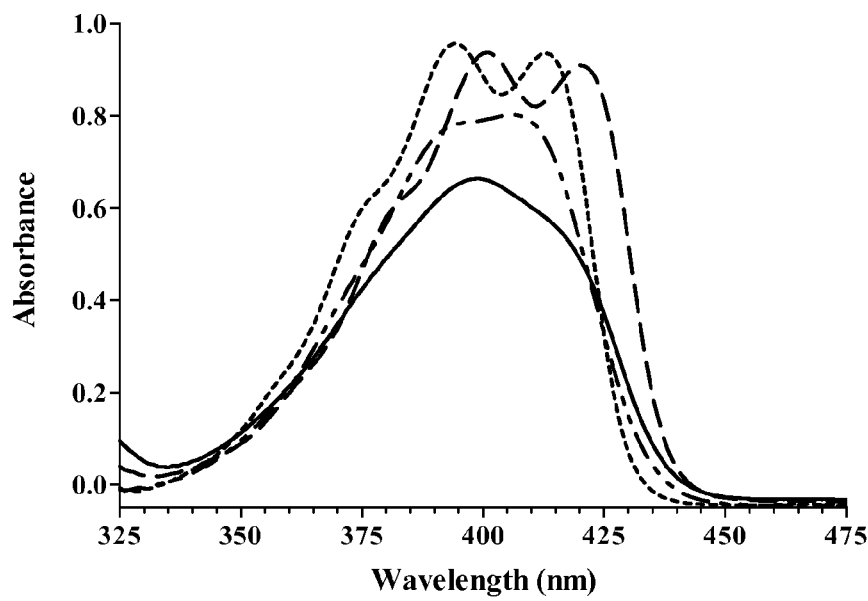
FIG. 1 shows the absorbance spectra (1A) and the emission spectra (1B) of four acridone dyes according to the present invention.
Figure 1B:
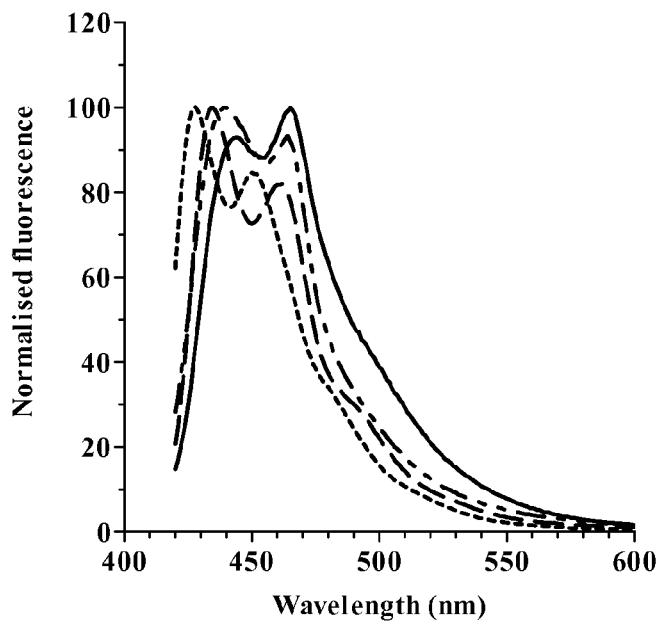
Figure 2:
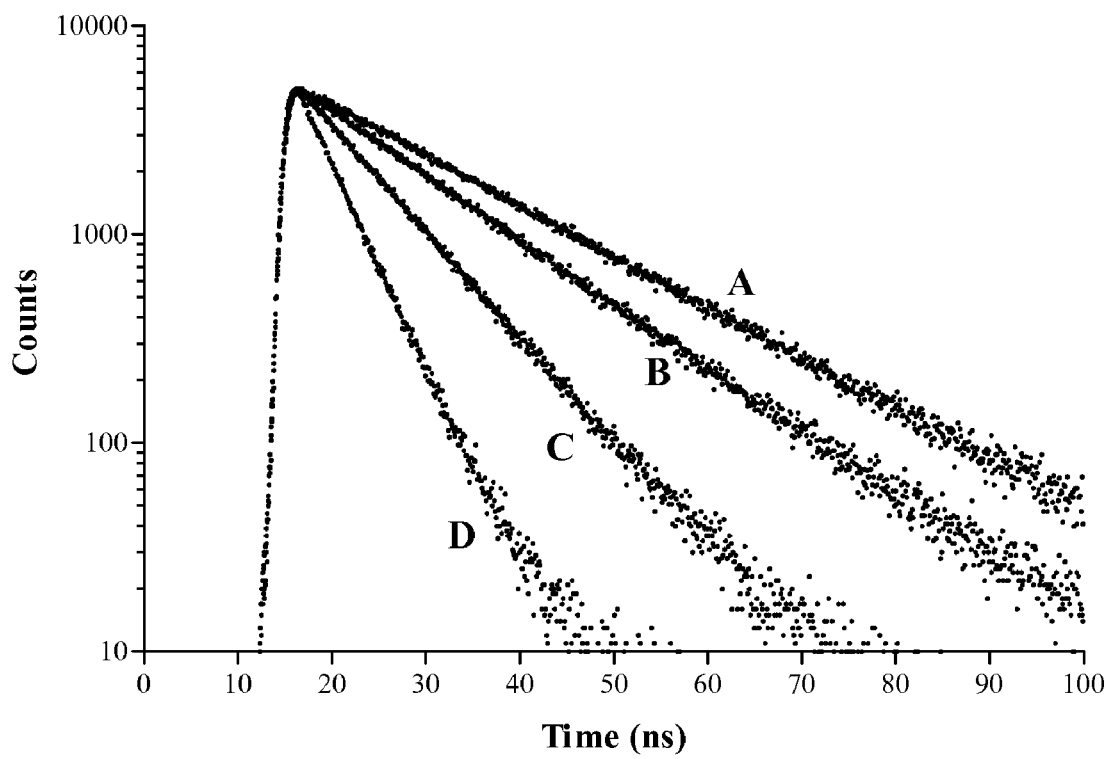
FIG. 2 shows the fluorescence lifetime decay plot of four acridone dyes according to the present invention, as follows.

Fluorescence lifetimes were determined by time-correlated single photon counting using an Edinburgh Instruments FL900CDT Time Resolved T-Geometry Fluorimeter. Samples were excited at 400 nm using a hydrogen arc lamp. Detection was at 450 nm. Deconvolution using a non-linear least squares algorithm gave the results shown in Table 2. FIG. 2 is a plot showing the fluorescence lifetimes of certain acridone dyes according to the invention.

TABLE 2

| Fluorescence Lifetimes | | |
|---|---|---|
| Compound | Solvent | Lifetime (nsecs) |
| N-(Succinyl)-2-amino-10H-acridine-9-one | water | 17.2 |
| 2-Carboxymethyl-7-chloro-9-oxo-9,10-acridine | MeOH | 16.8 |
| 6-(2,7-Disulphonato-9-oxo-9H-acridin-10-yl)hexanoic acid | water | 14.6 |
| 6-(9-Oxo-9H-acridin-10)hexanoic acid | water/MeOH 50/50 | 14.2 |
| 6-(2-Bromo-9-oxo-9H-acridin-10-yl)hexanoic acid | MeOH | 8.3 |
| 6-(2,7-Dibromo-9-oxo-9H-acridin-10-yl)hexanoic acid | MeOH | 4.5 |
| 6-(9-Oxo-9H-acridin-4-carboxamido)hexanoic acid | water/MeOH (50/50) | 4.2 |
| 2-Nitroacridone-7-sulphonic acid | water | non-fluorescent |
| 6-(2-Acetamido-9-oxo-9H-acridin-10-yl)hexanoic acid | water | 17 |
| 6-(2-Sulpho-9-oxo-9H-acridin-10-yl)hexanoic acid | water | 13.3 |
| 6-(2-Bromo-7-sulpho-9-oxo-9H-acridin-10-yl)hexanoic acid | water | 5.6 |
| 6-(2-Fluoro-9-oxo-9H-acridin-10-yl)hexanoic acid | water | 14 |
| 6-(2-Methoxy-9-oxo-9H-acridin-10-yl)hexanoic acid | water | 17 |

16. Protein Labelling

16.1 Preparation of 6-(9-oxo-9H-acridin-10-yl)hexanoic acid—bovine serum albumin (BSA) conjugate (Conjugate 1)

To 10 ml of bovine serum albumin (1 mg/ml in 0.1M carbonate buffer, pH9.3), 100 µl O—(N-succinimidyl)-6-(9-oxo-9H-acridin-10-yl)hexanoate (1 mg/100 µl in DMSO) was added dropwise whilst stirring. Gentle stirring continued for 1 hr at ambient temperature in a foil wrapped vial. Unconjugated dye was removed by overnight dialysis (12-14K MWCO) at 4° C. with at least 2 changes of PBS. Conjugate 1 was recovered and stored at 4° C.

16.2 Preparation of 6-(9-oxo-9H-acridin-4-carboxamido)hexanoic acid—rabbit serum albumin conjugate (Conjugate 2)

To 10 ml of rabbit serum albumin (1 mg/ml in 0.1M carbonate buffer, pH9.3), 100 µl O—(N-succinimidyl)-6-(9-oxo-9H-acridin-4-carboxamido)hexanoate (1 mg/100 µl in DMSO) was added dropwise whilst stirring. Gentle stirring continued for 1 hr at ambient temperature in a foil wrapped vial. Unconjugated dye was removed by overnight dialysis (12-14K MWCO) at 4° C. with at least 2 changes of PBS. Conjugate 2 was recovered and stored at 4° C.

16.3 Determination of the Fluorescence Lifetimes of Conjugates 1 and 2

The fluorescence lifetimes of a mixture of conjugates 1 and 2 were determined in PBS. The results are shown in FIG. 3. Deconvolution and curve fitting using a non-linear least-squares algorithm gave the results shown in Table 3.

TABLE 3

| Sample | Lifetime (ns) | Relative % |
|---|---|---|
| Conjugate 1 | 14.0 | 40.2 |
|  | 5.5 | 45.6 |
|  | 1.2 | 14.3 |
| Conjugate 2 | 4.6 | 49.4 |
|  | 1.2 | 35.0 |
|  | 19.3 | 15.6 |

16.4 Immunoprecipitation Assay

To 500 µl of PBS in a 1.5 ml centrifuge tube was added 200 µl conjugate 1 and 200 µl conjugate 2. After mixing, 450 µl was removed into a silica cuvette for determination of the fluorescence lifetime using excitation at 405 nm, emission at 450 nm by a time-correlated single photon counting technique (Edinburgh Analytical Instruments FL900CDT spectrometer). To the 450 µl in the centrifuge tube, 100 µl of anti-BSA antibody was added. After incubation for 30 min at 37° C., then 1 hr incubation at 4° C., the tube was centrifuged for 5 min in a bench-top centrifuge. The pellet was washed twice with ice-cold PBS, then re-suspended in 0.1M NaOH. The fluorescence lifetime of this solution was determined as above. The results are shown in FIG. 4. Deconvolution and curve fitting using a non-linear least-squares analysis algorithm gave the results shown in Table 4.

TABLE 4

Lifetime Fits for Immunoprecipitation Assay

| Sample | Lifetime (ns) | Relative % |
|---|---|---|
| Initial mixture | 14.7 | 33.3 |
|  | 5.0 | 47.5 |
|  | 0.9 | 19.2 |
| Re-suspended pellet | 13.1 | 70.3 |
|  | 4.7 | 22.8 |
|  | 0.7 | 6.9 |

The results show that the relative percentage of conjugate 1 (lifetime range 13-15 ns) has increased significantly in the pellet, as a result of the immunoprecipitation by the anti-BSA antibody. The proportion of conjugate 2 (lifetime range 4.5-5 ns) in the re-suspended pellet is correspondingly decreased, relative to the proportion in the initial mixture. Although the immunoprecipitation process was not completely efficient, analysis using fluorescence lifetime has enabled the resolution of two species (conjugate 1 and conjugate 2) in mixtures which are indistinguishable by their emission wavelength.

17. Fluorescence Lifetime Detection in Capillary Electrophoresis of Acridone Dye-Labelled DNA Fragments M13 DNA primers were labelled using standard techniques with each of four acridone dyes according to the present invention, i.e:
i) 6-(2-(acetylamino)-9-oxo-9H-acridin-10-yl)hexanoic acid,
ii) 6-(9-oxo-9H-acridin-10-yl)hexanoic acid,
iii) 6-(2-bromo-9-oxo-9H-acridin-10-yl)hexanoic acid, and
iv) 6-(9-oxo-9H-acridin-4-carboxamido)hexanoic acid.
The succinimidyl ester of each dye was conjugated to an amine-modified M13 forward sequencing primer in 0.1M carbonate pH 9.3/DMF (final composition 2:1). Purification by HPLC on a C18 column used a triethylammonium bicarbonate/MeCN solvent system.

Real-time fluorescence lifetime detection was achieved by interfacing a commercial multiharmonic Fourier transform (MHF) fluorescence lifetime instrument (Model 4850MHF, Spectronics Instruments, Rochester, N.Y.) to a Beckman P/ACE 5000 CE system (Li, L. et al, J. Chromatogr. B, (1997), 695, 85-92). The excitation source was a continuous wave violet diode laser that supplied 25-30 mW at 405 nm. The laser beam was focused onto the detection window of the capillary using either a 45 mm focusing lens or a 6.3× microscope objective with a focal length of 22 mm. The emission signal was collected by a 40× microscope objective. Emission was selected through a 435 nm long pass filter. A cross-correlation frequency of 9.4 Hz was used in the lifetime measurements, resulting in 9.4 phase and modulation measurements per second. Ten successive measurements were then averaged prior to data analysis to yield approximately one lifetime measurement per second. Scattered light from the capillary provided the lifetime reference.

Solutions of 0.5 mM dye-labelled primer in 100 mM Tris buffer, pH 8.6, were injected into the bare 75 µM internal diameter capillary for 10 s each at 10 kV injection voltage. The separation voltage was 18 kV (250 V/cm). The replaceable gel matrix contained 2% POP-6 gel in 3.5× POP-6 buffer. The lifetime electropherogram as shown in FIG. 5 was obtained for successive injections of M13 DNA primers labelled with each of the four dyes. The solid line is the intensity and the dots correspond to lifetimes recovered from a 1-component fit using non-linear least squares analysis software (Globals, Inc). The results show that the fluorescence lifetime (dots) coincides with the fluorescence intensity peaks (line) as the dye labelled M13 primers migrate past the detector.

18. Multiplexing Fluorescence Lifetime Determination

The following fluorescent acridone dye derivatives were prepared as 1 mg/ml stock solutions in methanol:
a) 6-(9-oxo-9H-acridin-10-yl)hexanoic acid;
b) 6-(2-bromo-9-oxo-9H-acridin-10-yl)hexanoic acid; and
c) 6-(9-oxo-9H-acridin-4-carboxamido)hexanoic acid.

The methanolic stock solutions were diluted (1/100) into 12% polyacrylamide mix which was allowed to polymerize directly in disposable cuvettes. Mixtures of the dyes were similarly prepared. The fluorescence lifetimes of samples containing single, or mixtures of dyes in polyacrylamide gel, were recorded by a time-correlated single photon counting technique (Edinburgh Analytical Instruments FL900CDT spectrometer). Samples were excited at 400 nm using a hydrogen arc lamp, detection was at 450 nm. Deconvolution using a non-linear least squares algorithm gave the results shown in Table 5.

TABLE 5

| Sample | Principal Lifetime (ns) | Relative % |
|---|---|---|
| a) 6-(9-oxo-9H-acridin-10-yl)hexanoic acid | 14.0 | 96.8 |
| b) 6-(2-bromo-9-oxo-9H-acridin-10-yl)hexanoic acid | 9.0 | 77.1 |
| c) 6-(9-oxo-9H-acridin-4-carboxamido)hexanoic acid | 3.6 | 74.4 |
| a) + c) | 14.0 | 74.5 |
|  | 3.9 | 25.5 |
| b) + c) | 9.5 | 49.7 |
|  | 4.0 | 50.3 |
| a) + b) + c) | 14.3 | 55.5 |
|  | 7.9 | 26.7 |
|  | 3.5 | 17.9 |

The results show that multiple lifetime components are reported when the dyes are analysed in PAGE. However, the principal lifetime component of each of the single dyes can still be distinguished in mixtures of the dyes in PAGE. Thus, with prior knowledge of the lifetime components present, the potential to multiplex fluorescence lifetimes has been demonstrated.

19. Co-Localisation of Bovine Serum Albumin (BSA) Labelled with Different Acridone Dyes Using SDS Page

19.1 Preparation of 6-(9-oxo-9H-acridin-4-carboxamido)hexanoic acid—bovine serum albumin (BSA) Conjugate (Conjugate 3)

To 1 ml of BSA (10.0 mg/ml in 0.1M NaHCO$_3$ solution) was added a solution of O—(N-succinimidyl)-6-(9-oxo-9H-acridin-4-carboxamido)hexanoate (lifetime 4 ns) (25 µl; 0.3125 mg/ml in DMSO). The resulting mixture was incubated at room temperature for 30 minutes with occasional mixing. A PD10 column (Amersham Biosciences) was equilibrated with 10 ml of phosphate buffered saline (PBS; pH 7.4). The dye-labelled BSA was added to the column, the column washed with PBS (2 ml) and then eluted with 3 ml of PBS. The eluate was collected to yield Conjugate 3.

19.2 Preparation of 6-(9-oxo-9H-acridin-10-yl)hexanoic acid—Bovine Serum Albumin (BSA) Conjugate (Conjugate 4)

To 1 ml of BSA (10.0 mg/ml in 0.1M NaHCO$_3$) was added a solution of O—(N-succinimidyl)-6-(9-oxo-9H-acridin-10-yl)hexanoate (lifetime 14 ns) (2 mg in 100 µl of DMSO). The resulting mixture was incubated at room temperature for 30 minutes with occasional mixing. A PD10 column (Amersham Biosciences) was equilibrated with 10 ml of phosphate buffered saline (PBS; pH 7.4). The dye-labelled BSA was added to the column, the column washed with PBS (2 ml) and then eluted with 3 ml of PBS. The eluate was collected to yield Conjugate 4.

19.3 Sample Preparation and Electrophoresis

Conjugates 3 and 4 prepared as above, were mixed together in a ratio of 2:1 in 0.05M Tris (20 µl); buffered to pH 7.5 with acetic acid containing 1% w/v sodium dodecyl sulphate, Bromophenol Blue (10 mg/100 ml) and dithiothrietol (154 mg/100 ml) (Amersham Biosciences). Protein samples were reduced by heating to 95° C. for 3 minutes. Electrophoresis was performed using a MultiPhor II flat bed electrophoresis system with ExcelGel SDS buffer strips (anode strip: 0.45 mol/Tris/acetate pH 6.6, 4 g/L SDS and 0.05 g/L Orange G; cathode strip: 0.08 mol/L Tris, 0.80 mol/L Tricine and 6.0 g/L SDS pH 7.1). Duplicate samples were applied to the surface of a pre-formed Excel 8-18 SDS PAGE gradient gel (Amersham Biosciences) using a paper sample application strip placed at locations corresponding with 96-well microplate centres required for scanning the gel. Molecular weight markers were run in separate lanes, so that part of the gel could be stained using Coomassie Blue to check the integrity of the samples, monitor molecular weight and to orientate the gel for lifetime scanning. Electrophoresis was initiated at constant current to a maximum voltage of 500V for 85 minutes with the flat bed temperature maintained at 15° C. Prior to scanning, the gel was fixed in aqueous solution of 25% methanol, 5% acetic acid v/v for at least 30 minutes. Following lifetime scanning, the gel was stained for 10-20 minutes in 0.1% Coomassie Blue G-250 in aqueous solution of 25% methanol, 5% acetic acid v/v and de-stained in aqueous solution of 25% methanol, 5% acetic acid v/v.

19.4 Scanning

Fixed gels were scanned with single wavelength laser excitation at 405 nm and the gel sampled at approximately 2 mm intervals along the axis of the electrophoretic separation. Data was analysed using a Bayesian algorithm to assign fluorescence intensity to fluorescence lifetimes of 2 ns (gel background); 4 ns (4 ns acridone dye); 6 ns (intrinsic BSA lifetime); and 14 ns (14 ns acridone dye).

FIG. 6 shows the 4 ns dye-labelled BSA and the 14 ns dye-labelled BSA (mixed in a ratio of 2:1) and co-electrophoresed in the same gel lane. Two peaks are resolved at 4 ns and 14 ns, both corresponding to the position of BSA relative to molecular weight markers. The two labelled BSA species are co-located but distinguishable by lifetime discriminated intensity. Both BSA species are resolved by the gel to the same location in the gel as indicated by reference to molecular weight markers and post electrophoresis staining (66 kD).

The above mentioned examples of conceivable embodiments are intended to illustrate the present invention and are not intended to limit the scope of protection claimed by the following claims.

The invention claimed is:

1. A method for labelling and detecting a biological material, the method comprising:
   i) adding to a liquid containing said biological material a fluorescent dye of formula:

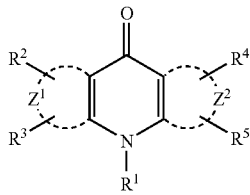

wherein:
   groups $R^2$ and $R^3$ are attached to the $Z^1$ ring structure and groups $R^4$ and $R^5$ are attached to the $Z^2$ ring structure;
   $Z^1$ and $Z^2$ independently represent the atoms necessary to complete one ring, two fused ring, or three fused ring aromatic or heteroaromatic systems, each ring having five or six atoms selected from carbon atoms and optionally no more than two atoms selected from oxygen, nitrogen and sulphur;
   at least one of groups $R^1$, $R^2$, $R^3$, $R^4$ and $R^5$ is the group -E-F where E is a spacer group having a chain from 1-60 atoms selected from the group consisting of carbon, nitrogen, oxygen, sulphur and phosphorus atoms and F is a target bonding group;
   when any of said groups $R^2$, $R^3$, $R^4$ and $R^5$ is not said group -E-F, said remaining groups $R^2$, $R^3$, $R^4$ and $R^5$ are independently selected from hydrogen, halogen, amide, hydroxyl, cyano, amino, mono- or di-$C_1$-$C_4$ alkyl-substituted amino, sulphydryl, carbonyl, carboxyl, $C_1$-$C_6$ alkoxy, acrylate, vinyl, styryl, aryl, heteroaryl, $C_1$-$C_{20}$ alkyl, aralkyl, sulphonate, sulphonic acid, quaternary ammonium and the group —$(CH_2—)_nY$; and,
   when group $R^1$ is not said group -E-F, it is selected from hydrogen, $C_1$-$C_{20}$ alkyl, aralkyl and the group —$(CH_2—)_nY$;
   Y is selected from sulphonate, sulphate, phosphonate, phosphate, quaternary ammonium and carboxyl; and n is an integer from 1 to 6;
   ii) incubating said dye with said target biological material under conditions suitable for labelling said biological material; and
   iii) detecting said labelled biological material by measurement of its fluorescence lifetime.

2. The method of claim 1, wherein said fluorescent dye has a fluorescence lifetime in the range from 2 to 30 nanoseconds.

3. The method of claim 1, wherein $Z^1$ and $Z^2$ independently represent the atoms necessary to complete a phenyl or a naphthyl ring structure.

4. The method of claim 1, wherein said target bonding group F comprises either:
   i) a reactive group selected from carboxyl, succinimidyl ester, sulpho-succinimidyl ester, isothiocyanate, maleimide, haloacetamide, acid halide, hydrazide, vinylsulphone, dichlorotriazine and phosphoramidite; or ii) a functional group selected from hydroxy, amino, sulphydryl, imidazole, carbonyl including aldehyde and ketone, phosphate and thiophosphate.

5. The method of claim 1, wherein said spacer group E is selected from:

—$(CHR')_p$—

—$\{(CHR')_q—O—(CHR')_r\}_s$—

—$\{(CHR')_q—NR'—(CHR')_r\}_s$—

—$\{(CHR')_q—(CH=CH)—(CHR')_r\}_s$—

—$\{(CHR')_q—Ar—(CHR')_r\}_s$—

—$\{(CHR')_q—CO—NR'—(CHR')_r\}_s$—

—$\{(CHR')_q—CO—Ar—NR'—(CHR')_r\}_s$— where R' is hydrogen, $C_1$-$C_4$ alkyl or aryl, which may be optionally substituted with sulphonate, Ar is phenylene, optionally substituted with sulphonate, p is 1-20, preferably 1-10, q is 0-10, r is 1-10 and s is 1-5.

6. The method of claim 1, wherein at least one of groups $R^1$, $R^2$, $R^3$, $R^4$ and $R^5$ comprises the group —$(CH_2—)_nY$, where Y is selected from sulphonate, sulphate, phosphonate, phosphate, quaternary ammonium and carboxyl and n is zero or an integer from 1 to 6.

7. The method of claim 1, wherein said biological material is selected from the group consisting of antibody, lipid, protein, peptide, carbohydrate, nucleotides which contain or are derivatized to contain one or more of an amino, sulphydryl, carbonyl, hydroxyl and carboxyl, phosphate and thiophosphate groups, and oxy or deoxy polynucleic acids which contain or are derivatized to contain one or more of an amino, sulphydryl, carbonyl, hydroxyl and carboxyl, phosphate and thiophosphate groups, microbial materials, drugs, hormones, cells, cell membranes and toxins.

* * * * *